(12) United States Patent
Spero et al.

(10) Patent No.: US 11,179,723 B2
(45) Date of Patent: *Nov. 23, 2021

(54) SYSTEM, FLUIDICS CARTRIDGE, AND METHODS FOR USING ACTUATED SURFACE-ATTACHED POSTS FOR PROCESSING CELLS

(71) Applicants: Redbud Labs, Inc., Research Triangle Park, NC (US); THE UNIVERSITY OF NORTH CAROLINA AT CHAPEL HILL, Chapel Hil, NC (US)

(72) Inventors: Richard Chasen Spero, Chapel Hill, NC (US); Jay Kenneth Fisher, Durham, NC (US); Richard Superfine, Chapel Hill, NC (US)

(73) Assignees: REDBUD LABS, INC., Research Triangle Park, NC (US); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/499,139

(22) PCT Filed: Mar. 23, 2018

(86) PCT No.: PCT/US2018/024151
§ 371 (c)(1),
(2) Date: Sep. 27, 2019

(87) PCT Pub. No.: WO2018/183126
PCT Pub. Date: Oct. 4, 2018

(65) Prior Publication Data
US 2020/0368747 A1    Nov. 26, 2020

Related U.S. Application Data

(60) Provisional application No. 62/477,927, filed on Mar. 28, 2017.

(51) Int. Cl.
*B01L 3/00* (2006.01)
*C12M 3/00* (2006.01)
*C12M 3/06* (2006.01)

(52) U.S. Cl.
CPC ... *B01L 3/502761* (2013.01); *B01L 3/502746* (2013.01); *C12M 23/16* (2013.01); *C12M 23/42* (2013.01)

(58) Field of Classification Search
CPC ......... B01F 13/0091; B01L 2200/0631; B01L 2200/0668; B01L 2300/088;
(Continued)

(56) References Cited

U.S. PATENT DOCUMENTS

2018/0266951 A1* 9/2018 Spero .................. B01F 13/0059

* cited by examiner

*Primary Examiner* — Jennifer Wecker
(74) *Attorney, Agent, or Firm* — E. Eric Mills; Nexsen Pruet, PLLC

(57) ABSTRACT

A cell processing system, fluidics cartridge, and methods for using actuated surface-attached posts for processing cells are disclosed. Particularly, the cell processing system includes a fluidics cartridge and a control instrument. The fluidics cartridge includes a cell processing chamber that has a micropost array therein, a sample reservoir and a wash reservoir that supply the cell processing chamber, and a waste reservoir and an eluent reservoir at the output of the cell processing chamber. A micropost actuation mechanism and a cell counting mechanism are provided in close proximity to the cell processing chamber. A method is provided of using the cell processing system to collect, wash, and recover cells. Another method is provided of using the cell processing system to collect, wash, count, and recover cells at a predetermined cell density.

25 Claims, 21 Drawing Sheets

(58) Field of Classification Search
CPC ..... B01L 2300/0883; B01L 2400/0406; B01L 2400/0415; B01L 2400/043; B01L 2400/086; B01L 3/502746; B01L 3/502761; C12M 23/16; C12M 23/42; C12M 41/48; F04B 17/03; F04B 19/006; F04B 19/22; F04B 43/043; F04D 33/00
See application file for complete search history.

SYSTEM, FLUIDICS CARTRIDGE, AND METHODS FOR USING ACTUATED SURFACE-ATTACHED POSTS FOR PROCESSING CELLS

TECHNICAL FIELD OF THE INVENTION

The presently disclosed subject matter relates generally to the processing of biological materials and more particularly to a system, fluidics cartridge, and methods for using actuated surface-attached posts for processing cells.

BACKGROUND

Currently, for biological analysis, cells are washed by centrifugation. For example, a 10 mL-sample can be spun in a centrifuge to form a cell pellet. Then the supernatant is removed and replaced with some other fluid. This process can be repeated multiple times depending on the desired purity of the background fluid. However, there are drawbacks to conventional cell washing by centrifugation. For example, the repeated wash cycles by centrifugation is a labor intensive process, and thus costly. Mainly because the centrifugation process has to be continuously monitored by a technician. Further, the centrifugation process is prone to other problems, like losing cells when pipetting. Additionally, with repeated washes the cell pellet can be harder and harder to keep compact and consequently cells can be lost.

SUMMARY OF THE INVENTION

In one embodiment, a cell processing system is provided comprising:
 a fluidics cartridge comprising:
 a cell processing chamber comprising a bottom substrate and a top substrate separated by the gap, wherein the cell processing chamber further comprises a micropost array, wherein the micropost array comprises a plurality of surface-attached microposts arranged on a micropost substrate, and wherein the micropost substrate is positioned atop the bottom substrate; and
 a control instrument;
wherein the surface-attached posts are configured for actuation in the presence of an actuation force, wherein no binding agents are disposed on or integrated with the surface-attached posts, the bottom substrate, the top substrate, or the micropost substrate, and wherein the bottom substrate and the top substrate are arranged atop a registration feature configured for mounting on the control instrument.

In some embodiments, the fluidics cartridge further comprises one or more sample reservoirs, one or more wash reservoirs, one or more supply cell processing chambers, one or more waste reservoirs, and one or more eluent reservoirs fluidly connected via an arrangement of fluid channels to the cell processing chamber. In other embodiments, a fluid control port is provided in each of the fluid channels. In other embodiments, the one or more sample reservoirs, the one or more wash reservoirs, the one or more supply cell processing chambers, the one or more waste reservoirs, and the one or more eluent reservoirs each comprise an inlet and an outlet. In other embodiments, a fluid control port is provided at the outlet of the sample reservoir, a fluid control port is provided at the outlet of the wash reservoir, a fluid control port is provided at the inlet of the waste reservoir, and a fluid control port is provided at the inlet of the eluent reservoir. In other embodiments, the fluid control ports comprise pinch valves. In other embodiments, a first pump is fluidly connected to the sample reservoir and a second pump is fluidly connected to the wash reservoir. In other embodiments, the first pump and the second pump are capable of supplying positive pressure and negative pressure to the cell processing chamber. In other embodiments, one or more of the sample reservoir, the wash reservoir, the waste reservoir, and the eluent reservoir comprise seals that are gas permeable but not liquid permeable.

In some embodiments, the control instrument comprises a base that houses one or more mechanisms for providing one or more actuation forces to the microposts, one or more mechanisms for counting cells in the cell processing chamber, one or more pneumatics for pumping and controlling fluids in the fluidics cartridge, and a controller. In other embodiments, the actuation force is selected from the group consisting of a magnetic field, a thermal field, a sonic field, an optical field, an electrical field, and a vibrational field.

In some embodiments, the control instrument comprises a platform configured to interface with the fluidics cartridge. In other embodiments, the platform comprises a plurality of fluid control ports positioned to correspond to the fluid channels of the fluidics cartridge. In other embodiments, each of the fluid control ports comprise a valve mechanism. In other embodiments, the valve mechanism is a pinch valve. In other embodiments, the platform further comprises an optical window substantially aligned with the cell processing chamber of the fluidics cartridge. In other embodiments, the one or more mechanisms for counting cells in the cell processing chamber is an optical imaging system. In other embodiments, the one or more mechanisms for counting cells in the cell processing chamber comprises measurement of electrical resistance, flow cytometry, image analysis, spectrophotometry, detection of fluorescence of fluorescently labeled cells, or combinations thereof. In other embodiments, the cell processing system is a standalone device.

In some embodiments, the cell processing system further comprises an automated robotics system for processing biological materials. In other embodiments, the automated robotics system for processing biological materials comprises a multi-well plate. In other embodiments, the multi-well plate is selected from the group consisting of a 12-well plate, a 24-well plate, and a 96-well plate. In other embodiments, dimensions of the registration feature of the fluidics cartridge substantially correspond to dimensions of the multi-well plate. In other embodiments, the automated robotics system for processing biological materials further comprises one or more pipettes for processing fluids from the multi-well plate. In other embodiments, the automated robotics system for processing biological materials further comprises a pipette for processing fluids from the eluent reservoir of the fluidics cartridge.

In some embodiments, the microposts are formed of polydimethylsiloxane (PDMS). In other embodiments, the microposts range in length from about 1 µm to about 100 µm. In other embodiments, the microposts range in diameter from about 0.1 µm to about 10 µm. In other embodiments, the microposts have a cross-sectional shape selected from the group consisting of circular, ovular, square, rectangular, and triangular. In other embodiments, the microposts are oriented substantially normal to the plane of the substrate. In other embodiments, the microposts are oriented at an angle α with respect to normal of the plane of the substrate. In other embodiments, the microposts are oriented at a pitch of from about 0 µm to about 50 µm.

In some embodiments, the cell processing system further comprises a controller capable of executing program instructions. In other embodiments, the cell processing system further comprises a user interface. In other embodiments, the cell processing system further comprises a communications interface. In other embodiments, the cell processing system further comprises a power source.

In some embodiments, a method is provided for processing cells comprising the use of any of the cell processing systems described herein, comprising the steps of:

(a) introducing a sample fluid to the sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell wash cycle comprising flowing wash buffer solution out of the wash reservoir, through cell processing chamber, and into the waste reservoir, wherein the cells remain precipitated onto the micropost substrate amongst the surface-attached microposts, and wherein no actuation forces are applied to the surface-attached microposts;

(e) repeating step (d) as needed to wash the cells precipitated onto the micropost substrate amongst the surface-attached microposts;

(f) performing a cell recovery cycle comprising flowing wash buffer solution through the cell processing chamber, wherein actuation forces are applied to the surface-attached microposts to resuspend the cells into the flowing wash buffer solution, thereby producing a cell-containing eluent; and (g) flowing the cell-containing eluent into the eluent reservoir.

In some embodiments, a method is provided for processing cells comprising the use of any of the cell processing systems described herein, comprising the steps of:

(a) introducing a sample fluid to the sample reservoir, wherein the sample fluid comprises cells, and wherein the cells are suspended in the sample fluid;

(b) flowing the sample fluid into the cell processing chamber while the surface-attached microposts are actuated, wherein the sample fluid is flowed at rate slow enough that the cells are not pushed out of the cell processing chamber;

(c) performing a cell wash cycle comprising flowing wash buffer solution out of the wash reservoir into the cell processing chamber, wherein actuation forces are applied to the surface-attached microposts, and further wherein the wash buffer solution is flowed at a rate slow enough that the cells are not pushed out of the cell processing chamber;

(d) performing a cell culture cycle comprising flowing cell culture media out of the cell culture media reservoir into the cell processing chamber, wherein actuation forces are applied to the surface-attached microposts, and further wherein the cell culture media is flowed at a rate slow enough that the cells are not pushed out of the cell processing chamber;

(e) performing a cell recovery cycle comprising flowing wash buffer solution through the cell processing chamber, wherein actuation forces are applied to the surface-attached microposts, and further wherein the wash buffer solution is flowed at a rate fast enough that the cells are not pushed out of the cell processing chamber; and (f) flowing the cell-containing eluent into the eluent reservoir. In some embodiments, the method further comprises the step of performing a cell counting operation with the cell counting mechanism to determine the number of cells in the cell processing chamber, wherein the cell counting operation is performed before the cell recovery cycle step.

In some embodiments, a method is provided for processing cells comprising the use of any of the cell processing systems described herein, comprising the steps of, comprising the steps of:

(a) introducing a sample fluid to the sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell wash cycle comprising flowing wash buffer solution out of the wash reservoir, through cell processing chamber, and into the waste reservoir, wherein the cells remain precipitated onto the micropost substrate amongst the surface-attached microposts, and wherein no actuation forces are applied to the surface-attached microposts;

(e) repeating step (d) as needed to wash the cells precipitated onto the micropost substrate amongst the surface-attached microposts;

(f) performing a cell culture cycle by flowing cell culture media into cell processing chamber while microposts are not actuated and providing time and conditions necessary for cell growth, expansion, and maintenance;

(g) performing a cell recovery cycle comprising flowing wash buffer solution through the cell processing chamber, wherein actuation forces are applied to the surface-attached microposts to resuspend the cells into the flowing wash buffer solution, thereby producing a cell-containing eluent; and (h) flowing the cell-containing eluent into the eluent reservoir. In some embodiments, the method further comprises the step of performing a cell counting operation with the cell counting mechanism to determine the number of cells in the cell processing chamber, wherein the cell counting operation is performed before the cell recovery cycle step.

In some embodiments, a method is provided for processing cells comprising the use of any of the cell processing systems described herein, comprising the steps of:

(a) introducing a sample fluid to the sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell wash cycle comprising flowing wash buffer solution out of the wash reservoir, through cell processing chamber, and into the waste reservoir, wherein the cells remain precipitated onto the micropost substrate amongst the surface-attached microposts, and wherein no actuation forces are applied to the surface-attached microposts;

(e) repeating step (d) as needed to wash the cells precipitated onto the micropost substrate amongst the surface-attached microposts;

(f) performing a cell counting operation with the cell counting mechanism to determine the number of cells in the cell processing chamber;

(g) performing a cell recovery cycle comprising flowing wash buffer solution through the cell processing chamber, wherein actuation forces are applied to the surface-attached microposts to resuspend the cells into the flowing wash buffer solution, thereby producing a cell-containing eluent; and (h) flowing the cell-containing eluent into the eluent reservoir.

In some embodiments, a method is provided for processing cells comprising the use of any of the cell processing systems described herein, comprising the steps of:

(a) introducing a sample fluid to the sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell lysis cycle, wherein actuation forces are applied to the surface-attached microposts to produce a beating motion by the surface-attached microposts, thereby producing a lysed cell-containing eluent; and (e) flowing the lysed cell-containing eluent into the eluent reservoir.

In some embodiments, a method is provided for processing cells comprising the use of any of the cell processing systems described herein, comprising the steps of:

(a) introducing a sample fluid to the sample reservoir, wherein the sample fluid comprises cells, and wherein the cells are suspended in the sample fluid;

(b) flowing the sample fluid into the cell processing chamber while the surface-attached microposts are actuated, wherein the sample fluid is flowed at rate slow enough that the cells are not pushed out of the cell processing chamber;

(c) performing a cell wash cycle comprising flowing wash buffer solution out of the wash reservoir, through the cell processing chamber, and into the waste reservoir, wherein actuation forces are applied to the surface-attached microposts, and further wherein the wash buffer solution is flowed at a rate slow enough that the cells are not pushed out of the cell processing chamber;

(d) performing a cell recovery cycle comprising flowing wash buffer solution through the cell processing chamber, wherein actuation forces are applied to the surface-attached microposts, and further wherein the wash buffer solution is flowed at a rate fast enough that the cells are not pushed out of the cell processing chamber; and (e) flowing the cell-containing eluent into the eluent reservoir.

In some embodiments, within the presently disclosed methods, the sample fluid comprises cells comprising clumps of cells, wherein the cells comprising clumps of cells are suspended in the sample fluid, and wherein step (b) further comprises applying actuation forces to the surface-attached microposts to break up the clumps of cells. In other embodiments, within the presently disclosed methods, prior to step (a), the sample fluid is produced by a cell concentration process comprising centrifuging a sample comprising cells to produce a cell pellet, followed by resuspending cells in the cell pellet in solution to produce the sample fluid.

In some embodiments, any of the cell processing systems described herein further comprise a microarray on the top substrate opposing the microposts, wherein the microarray is functionalized with analyte capture elements. In other embodiments, methods for processing cells are provided comprising the use of this cell processing system, comprising the steps of:

(a) introducing a sample fluid to the sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) flowing a lysis buffer into the cell processing chamber, thereby producing lysed cells and analytes; and (e) applying actuation forces to the surface-attached microposts to mix the lysed cells and analytes in the cell processing chamber, wherein analytes bind to the analyte capture elements of the microarray.

In some embodiments, processing systems described herein further comprise a cell concentration module. In other embodiments, methods for processing cells are provided comprising the use of this cell processing system, comprising the steps of:

(a) introducing a sample fluid to the sample reservoir, wherein the sample fluid comprises cells, and wherein the cells are suspended in the sample fluid;

(b) flowing the sample fluid into the cell concentration module and performing a cell concentration process to produce a concentrated sample fluid; and (c) flowing the concentrated sample fluid into the cell processing chamber for further processing.

In some embodiments, processing systems described herein further comprise a micropost array that comprises a flow path formed by the absence of microposts. In other embodiments, at least some portion of the flow path is curved and configured to aggregate cells at the outside of curves such that the cells precipitate and/or are pushed into the microposts. In other embodiments, the flow path is serpentine-shaped. In other embodiments, the flow path is spiral-shaped. In other embodiments, methods are provided for making these cell processing systems, wherein the method comprises fabricating the micropost array in a high density and using a tool to crush unwanted microposts to form the flow path.

In some embodiments, processing systems described herein further comprise a micropost array that comprises arrangements of micropost barriers configured to trap cells such that the cells precipitate and/or are pushed into the microposts. In other embodiments, the micropost barriers are arc-shaped, U-shaped, V-shaped, or bar-shaped.

In some embodiments, processing systems described herein further comprise features on the top substrate opposing the microposts, wherein the features are configured to assist cells to precipitate out of solution and/or facilitate microfludic cell separation. In other embodiments, the features are arranged in a herringbone configuration.

In some embodiments, processing systems described herein further comprise one or more electrodes provided in the bottom substrate, the top substrate, or both the bottom substrate and the top substrate.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

The features and advantages of the present invention will be more clearly understood from the following description taken in conjunction with the accompanying drawings, which are not necessarily drawn to scale, and wherein.

DETAILED DESCRIPTION

Figure 1:
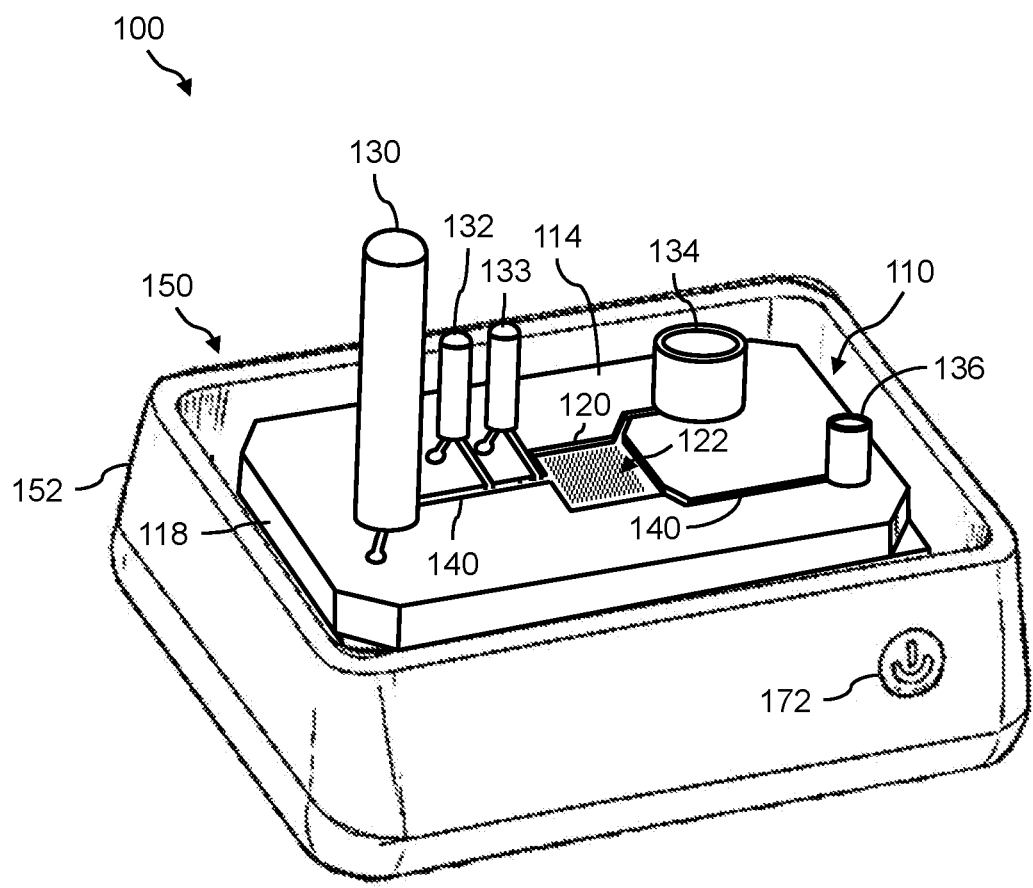
FIG. 1 illustrates a perspective view of an example of the presently disclosed cell processing system that uses actuated surface-attached posts for processing cells.

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a cell processing system, fluidics cartridge, and methods for using actuated surface-attached posts for processing cells. The cell processing system, fluidics cartridge, and methods provide ways of processing cells that (1) do not involve binding and (2) rely on fluidics. Examples of processes that can be performed using the presently disclosed cell processing system, fluidics cartridge, and methods include, but are not limited to, cell concentration, cell collection, cell filtration, cell washing, cell counting, cell recovery, cell lysis, cell de-clumping, and the like. Particularly, the presently disclosed cell processing system, fluidics cartridge, and methods are well-suited for the sample preparation process.

In some embodiments, the presently disclosed cell processing system includes a fluidics cartridge that sits atop a control instrument. The fluidics cartridge includes a cell processing chamber that has a micropost array therein, a sample reservoir and a wash reservoir that supply the cell processing chamber, and a waste reservoir and an eluent reservoir at the output of the cell processing chamber. In other embodiments, the fluidics cartridge can include multiple sample reservoirs, multiple wash reservoirs, multiple waste reservoirs, and multiple eluent reservoirs. In yet other embodiments, in fluidics cartridge, a cell concentration module can be provided in advance of (i.e., upstream) of the cell processing chamber.

The cell processing means utilize an array of surface-attached microposts (e.g., a micropost array). As used herein, the terms "surface-attached post" or "surface-attached micropost" or "surface-attached structure" are used interchangeably. Generally, a surface-attached structure has two opposing ends: a fixed end and a free end. The fixed end may be attached to a substrate by any suitable means, depending on the fabrication technique and materials employed. The fixed end may be "attached" by being integrally formed with or adjoined to the substrate, such as by a microfabrication process. Alternatively, the fixed end may be "attached" via a bonding, adhesion, fusion, or welding process. The surface-attached structure has a length defined from the fixed end to the free end, and a cross-section lying in a plane orthogonal to the length. For example, using the Cartesian coordinate system as a frame of reference, and associating the length of the surface-attached structure with the z-axis (which may be a curved axis), the cross-section of the surface-attached structure lies in the x-y plane.

Generally, the cross-section of the surface-attached structure may have any shape, such as rounded (e.g., circular, elliptical, etc.), polygonal (or prismatic, rectilinear, etc.), polygonal with rounded features (e.g., rectilinear with rounded corners), or irregular. The size of the cross-section of the surface-attached structure in the x-y plane may be defined by the "characteristic dimension" of the cross-section, which is shape-dependent. As examples, the characteristic dimension may be diameter in the case of a circular cross-section, major axis in the case of an elliptical cross-section, or maximum length or width in the case of a polygonal cross-section. The characteristic dimension of an irregularly shaped cross-section may be taken to be the dimension characteristic of a regularly shaped cross-section that the irregularly shaped cross-section most closely approximates (e.g., diameter of a circle, major axis of an ellipse, length or width of a polygon, etc.).

A surface-attached structure as described herein is movable (flexible, deflectable, bendable, etc.) relative to its fixed end or point of attachment to the substrate. To facilitate its movability, the surface-attached structure may include a flexible body composed of an elastomeric (flexible) material, and may have an elongated geometry in the sense that the dominant dimension of the surface-attached structure is its length—that is, the length is substantially greater than the characteristic dimension. Examples of the composition of the flexible body include, but are not limited to, elastomeric materials such as polydimethylsiloxane (PDMS).

The surface-attached structure is configured such that the movement of the surface-attached structure relative to its fixed end may be actuated or induced in a non-contacting manner, specifically by an applied magnetic or electric field of a desired strength, field line orientation, and frequency (which may be zero in the case of a magnetostatic or electrostatic field). To render the surface-attached structure movable by an applied magnetic or electric field, the surface-attached structure may include an appropriate metallic component disposed on or in the flexible body of the surface-attached structure. To render the surface-attached structure responsive to a magnetic field, the metallic component may be a ferromagnetic material such as, for example, iron, nickel, cobalt, or magnetic alloys thereof, one non-limiting example being "alnico" (an iron alloy containing aluminum, nickel, and cobalt). To render the surface-attached structure responsive to an electric field, the metallic component may be a metal exhibiting good electrical conductivity such as, for example, copper, aluminum, gold, and silver, and well as various other metals and metal alloys. Depending on the fabrication technique utilized, the metallic component may be formed as a layer (or coating, film, etc.) on the outside surface of the flexible body at a selected region of the flexible body along its length. The layer may be a continuous layer or a densely grouped arrangement of particles. Alternatively, the metallic component may be formed as an arrangement of particles embedded in the flexible body at a selected region thereof.

Accordingly, the application of a magnetic or electric field actuates the surface-attached microposts into movement. For example, the actuation occurs by contacting cell processing chamber with the control instrument comprising elements that provide an "actuation force," such as a magnetic or electric field. Accordingly, the control instrument includes, for example, any mechanisms for actuating the microposts (e.g., magnetic system), any mechanisms for counting the cells (e.g., imaging system), the pneumatics for pumping the fluids (e.g., pumps, fluid ports, valves), and a controller (e.g., microprocessor).

Additionally, in one example, the presently disclosed cell processing system can be a standalone device used in a sample preparation process. However, in another example, the presently disclosed cell processing system can be integrated into an automated sample preparation process, such as into a robotics system for processing biological materials. The robotics system can be, for example, a 12-well plate, 24-well plate, or 96-well plate polymerase chain reaction (PCR) system. In another example, the robotics system can be the Tecan robotics system used for sample prep available from Tecan Group Ltd., Switzerland.

An example of a method of using the presently disclosed cell processing system may include the steps of (1) flowing a cell-containing sample fluid into the cell processing chamber, (2) allowing the cells to precipitate out by gravity onto the chamber floor (i.e., the micropost substrate) and amongst the microposts while the microposts are not actuated, (3) performing a cell wash cycle by flowing a wash buffer solution through the cell processing chamber while the microposts are not actuated, and (4) performing a cell recovery cycle by flowing the wash buffer solution through the cell processing chamber while at the same time actuating the microposts in order to resuspend the cells into the flow.

Another example of a method of using the presently disclosed cell processing system may include the steps of (1) flowing a cell-containing sample fluid into the cell processing chamber, (2) allowing the cells to precipitate out by gravity onto the chamber floor (i.e., the micropost substrate) and amongst the microposts while the microposts are not actuated, (3) performing a cell wash cycle by flowing a wash buffer solution through the cell processing chamber while the microposts are not actuated, (4) performing a cell counting operation to determine the number of cells in the cell processing chamber, and (5) performing a cell recovery cycle by flowing the wash buffer solution through the cell processing chamber at a certain flow rate while at the same time actuating the microposts in order to resuspend the cells into the flow at a certain cell density (e.g., 15 cells/uL).

Figure 2:
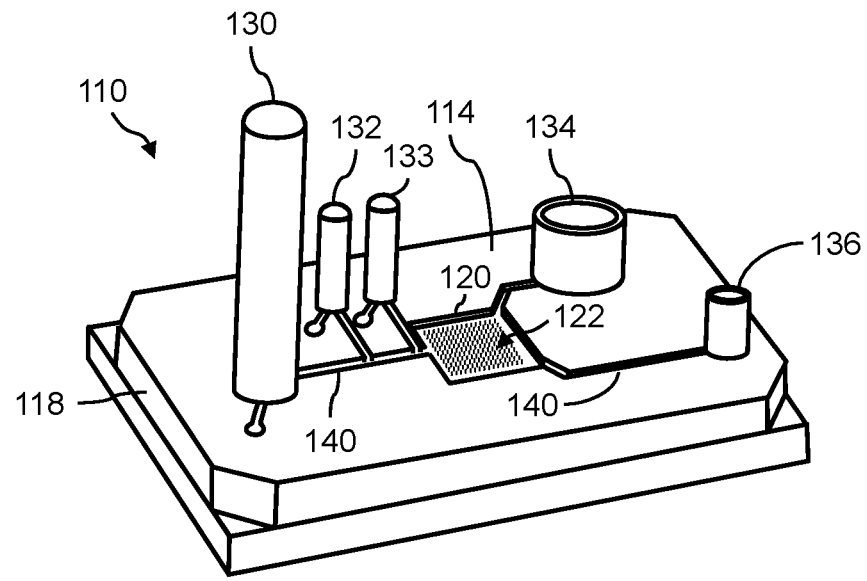
FIG. 2 illustrates an exploded perspective view of the presently disclosed cell processing system.
Figure 2:
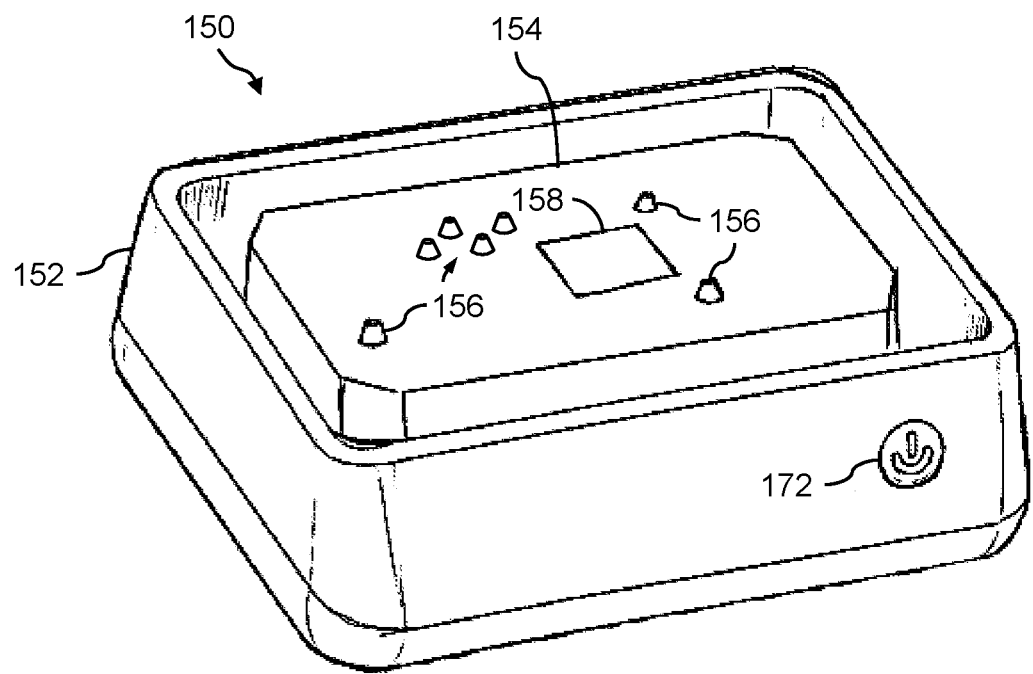

FIG. 1 illustrates a perspective view of an example of the presently disclosed cell processing system 100 that uses actuated surface-attached posts for processing cells, while FIG. 2 shows an exploded perspective view of cell processing system 100. Cell processing system 100 includes a fluidics cartridge 110 that mounts atop a control instrument 150. In cell processing system 100, fluidics cartridge 110 and control instrument 150 provides ways of processing cells that (1) do not involve binding and (2) rely on fluidics. Examples of processes that can be performed using cell processing system 100 include, but are not limited to, cell concentration, cell collection, cell filtration, cell washing, cell counting, cell recovery, cell lysis, cell de-clumping, and the like.

Figure 4:
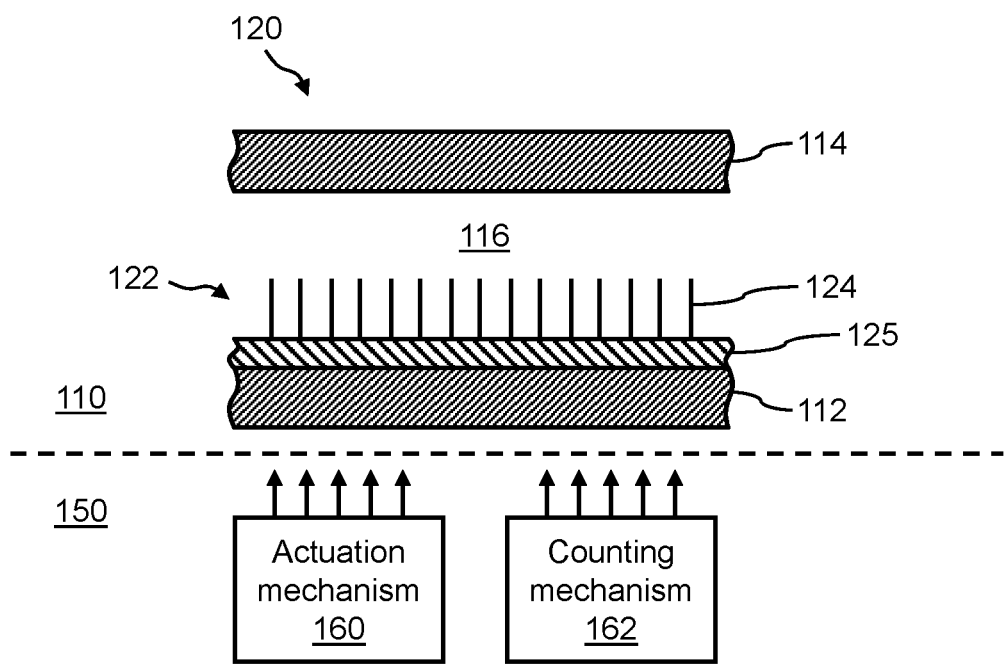
FIG. 4 illustrates a side view of a portion of a cell processing chamber of the presently disclosed cell processing system, wherein the cell processing chamber includes a micropost array.

Fluidics cartridge 110 includes a bottom substrate 112 and a top substrate 114 separated by a gap 116 (see FIG. 4). Bottom substrate 112 and top substrate 114 are arranged atop a registration feature 118 for mounting on control instrument 150. Fluidics cartridge 110 includes a cell processing chamber 120. A micropost array 122 is provided in cell processing chamber 120. Micropost array 122 includes a plurality of surface-attached microposts 124 arranged on a micropost substrate 125. In cell processing system 100, the cell processing means uses micropost array 122, which is the array of surface-attached microposts 124. The application of a magnetic or electric field actuates the surface-attached microposts 124 into movement. More details of micropost array 122 and microposts 124 are shown and described hereinbelow with reference to FIG. 4, FIG. 5A, FIG. 5B, FIG. 6A through FIG. 6D, FIG. 7A, and FIG. 7B.

In fluidics cartridge 110, a sample reservoir 130, a wash reservoir 132, and a cell culture media reservoir 133 supply cell processing chamber 120, and a waste reservoir 134 and an eluent reservoir 136 are at the output of cell processing chamber 120. Cell processing chamber 120, sample reservoir 130, wash reservoir 132, cell culture media reservoir 133, waste reservoir 134, and eluent reservoir 136 are fluidly connected via an arrangement of fluid channels 140. In other embodiments, fluidics cartridge 110 can include multiple sample reservoirs 130, multiple wash reservoirs 132, multiple cell culture media reservoirs 133, multiple waste reservoirs 134, and multiple eluent reservoirs 136.

Sample reservoir 130 holds the cell-containing sample fluid to be processed. Sample reservoir 130 can be any size ranging, for example, from a few 10s of milliliters (mL) to a few hundred microliters (μL). In one example, sample reservoir 130 holds about 200 μL of sample fluid.

Wash reservoir 132 holds, for example, a volume of wash buffer solution. Wash reservoir 132 can be any size depending on the amount of wash solution needed in the processes of cell processing system 100.

Cell culture media reservoir 133 holds, for example, a volume of cell culture media. Cell culture media reservoir 133 can be any size depending on the amount of cell culture media needed in the processes of cell processing system 100. The cell culture medium may be any medium that contains components necessary for the growth, expansion, and/or maintenance of cells in culture, for example one or more carbon sources (e.g., glucose/glutamine), one or more amino acids, one or more vitamins, a balances salt solution to maintain optimum osmotic pressure within the cells, a pH indicator, a pH buffer for maintaining a balanced pH in the media, oxygen, one or more other nutrients necessary for the survival of the cells, and/or one or more substances that promote stimulation for differentiation of the cells into desired cells. A medium containing cells is also called a cell suspension. The term "medium" is used hereinafter without distinguishing a medium and a cell suspension.

Waste reservoir 134 holds any waste fluid generated in the processes of cell processing system 100.

Eluent reservoir 136 holds the output eluent fluid generated in the processes of cell processing system 100, wherein the eluent can be used in any downstream processes.

Venting (not shown) of sample reservoir 130, wash reservoir 132, cell culture media reservoir 133, waste reservoir 134, and/or eluent reservoir 136 can be accomplished using, for example, seals that are gas permeable but not liquid permeable.

Figure 9:
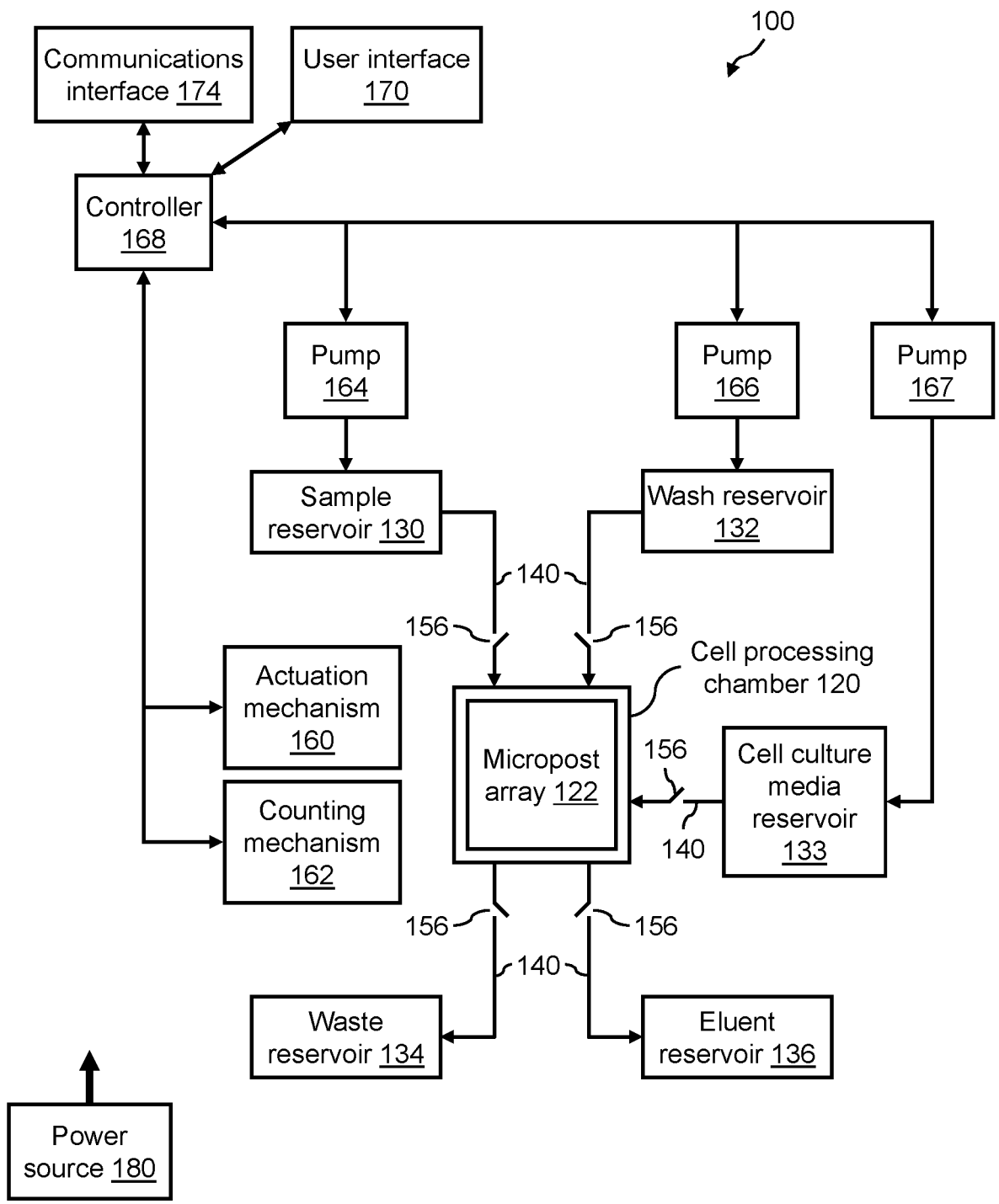
FIG. 9 illustrates a block diagram of an example of the presently disclosed cell processing system.

Control instrument 150 includes a base 152 that houses any mechanisms for actuating microposts 124 of micropost array 122 (see FIG. 4 and FIG. 9), any mechanisms for counting cells in cell processing chamber 120 (see FIG. 4 and FIG. 9), the pneumatics for pumping and controlling the fluids (see FIG. 9), and a controller (see FIG. 9).

Control instrument 150 includes a platform 154 that interfaces with fluidics cartridge 110. A plurality of fluid control ports 156 (see FIG. 2) is provided in platform 154. The positions of fluid control ports 156 correspond to the positions of fluid channels 140 of fluidics cartridge 110. Fluid control ports 156 can be any type of valve mechanism for controlling the flow out of sample reservoir 130, wash reservoir 132, and cell culture media reservoir 133 and for controlling the flow into waste reservoir 134 and eluent reservoir 136. In one example, fluid control ports 156 are pinch valves.

Optionally, an optical window 158 is provided in platform 154, wherein the position of optical window 158 substantially aligns with the position of cell processing chamber 120 of fluidics cartridge 110. Optical window 158 can be, for example, a transparent glass or plastic window. Optical window 158 is required when the mechanism for counting cells in cell processing chamber 120 is, for example, an optical imaging system.

Figure 3:
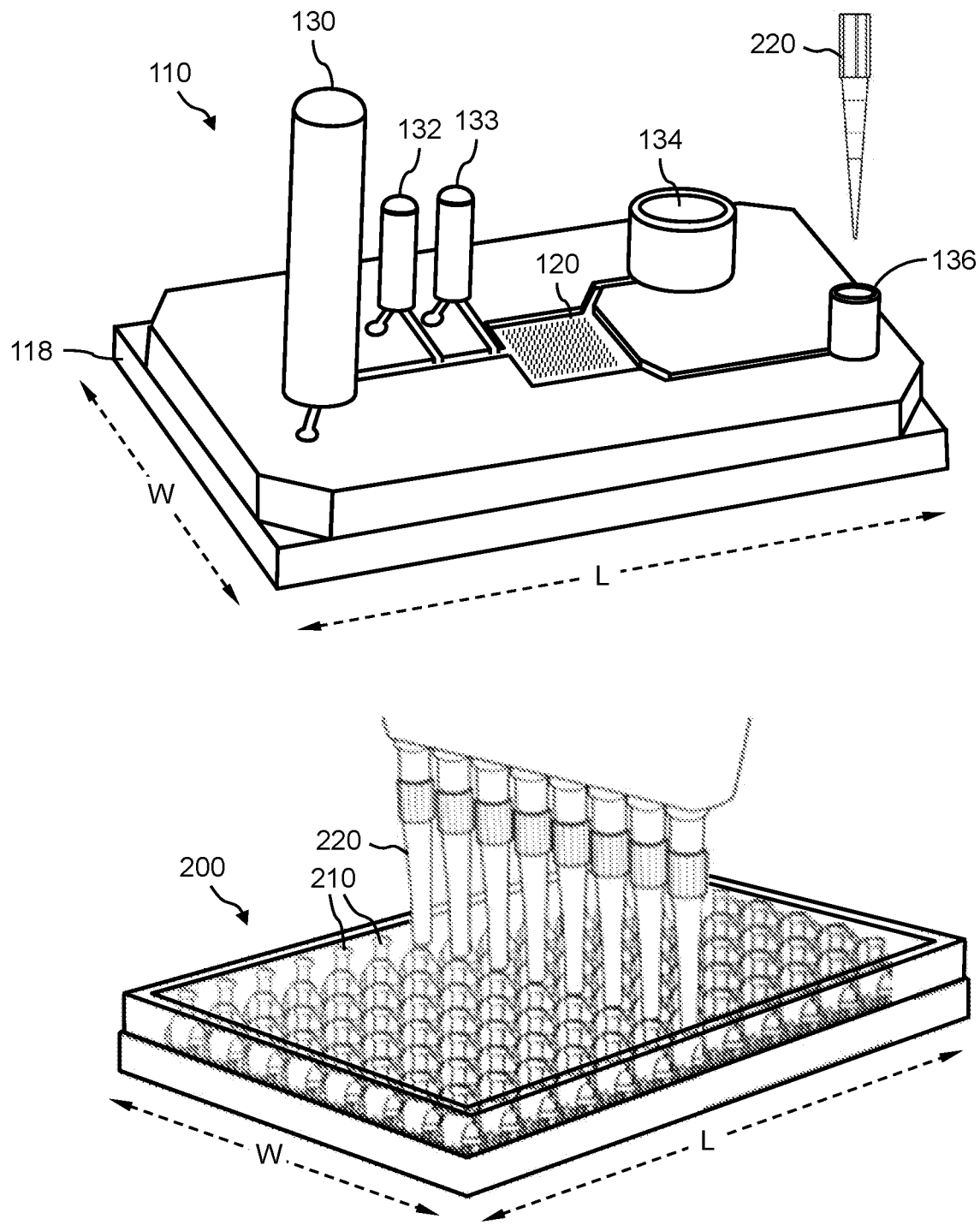
FIG. 3 illustrates a perspective view showing a size correlation of a fluidics cartridge of the presently disclosed cell processing system and a standard 96-well plate.

In one example, the presently disclosed cell processing system 100 can be a standalone device. However, in another example, the presently disclosed cell processing system 100 can be integrated into, for example, an automated robotics system for processing biological materials that uses standard microplate formats, such as a 12-well plate, 24-well plate, or 96-well plate. For example and referring now to FIG. 3, the size (i.e., dimensions) of registration feature 118 of fluidics cartridge 110 can substantially correspond to the size (i.e., dimensions) of a standard multi-well plate of a robotics system. For example, FIG. 3 shows a 96-well plate 200 that includes 96 wells 210. The 96-well plate 200 has a length L and a width W. Similarly, registration feature 118 of fluidics cartridge 110 has a length L and a width W. In one example, the length L of both the 96-well plate 200 and the fluidics cartridge 110 is about 125 mm. Further, the width W of both the 96-well plate 200 and the fluidics cartridge 110 is about 100 mm. FIG. 3 also shows pipettes 220 for processing fluids of the 96-well plate 200. Similarly, a pipette 220 can be used to process fluids from eluent reservoir 136 of fluidics cartridge 110.

FIG. 4 illustrates a side view of a portion of a cell processing chamber 120 of the presently disclosed cell processing system 100, wherein cell processing chamber 120 includes micropost array 122, which is the array of microposts 124. Cell processing chamber 120 provides a "flowcell" type of chamber. For example, a flowcell can be any chamber comprising a solid surface across which one or more liquids can be flowed, wherein the chamber has at least one inlet and at least one outlet. FIG. 4 shows a portion of micropost array 122, which includes the surface-attached microposts 124 arranged on micropost substrate 125.

Cell processing chamber 120 can be sized to hold any volume of fluid. The height of cell processing chamber 120 can be, for example, from about 50 μm to about 100 μm. In one example, cell processing chamber 120 is sized to hold about 200 μL of fluid. In this example, cell processing chamber 120 can be about 4.5 cm long, about 4.5 cm wide, and about 100 μm high.

Referring again to FIG. 4, in cell processing system 100, an actuation mechanism 160 of control instrument 150 is arranged in close proximity to cell processing chamber 120 of fluidics cartridge 110. Actuation mechanism 160 can be any mechanism for actuating microposts 124 of micropost array 122 in fluidics cartridge 110. As used herein, the term "actuation force" refers to the force applied to microposts 124. Actuation mechanism 160 is used to generate an actuation force in proximity to micropost array 122 that compels at least some of microposts 124 to exhibit motion. The actuation force may be, for example, magnetic, thermal, sonic, and/or electric force. Further, the actuation force may be applied as a function of frequency or amplitude, or as an impulse force (i.e., a step function). Similarly, other actuation forces may be used without departing from the scope of the present subject matter, such as fluid flow across micropost array 122.

By actuating microposts 124 and causing motion thereof, the sample fluid (not shown) in gap 116 is in effect stirred or caused to flow or circulate within gap 116 of cell processing chamber 120. Micropost array 122 that includes the arrangement of microposts 124 is based on, for example, the microposts described in the U.S. Pat. No. 9,238,869, entitled "Methods and systems for using actuated surface-attached posts for assessing biofluid rheology," issued on Jan. 19, 2016; the entire disclosure of which is incorporated herein by reference. The '869 patent describes methods, systems, and computer readable media for using actuated surface-attached posts for assessing biofluid rheology. According to one aspect, a method of the '869 patent for testing properties of a biofluid specimen includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method of the '869 patent further includes measuring the motion of at least one of the microposts in response to the actuation force and determining a property of the specimen based on the measured motion of the at least one micropost.

In one example, according to the '869 patent, microposts 124 and micropost substrate 125 of micropost array 122 can be formed of polydimethylsiloxane (PDMS). Further, microposts 124 may include a flexible body and a metallic component disposed on or in the body, wherein application of a magnetic or electric field actuates microposts 124 into movement relative to the surface to which they are attached. In this example, the actuation force generated by actuation mechanism 160 is a magnetic and/or electrical actuation force. More details of micropost array 122 and microposts 124 are shown and described hereinbelow with reference to FIG. 5A through FIG. 7B.

Referring yet again to FIG. 4, in cell processing system 100, a counting mechanism 162 of control instrument 150 are arranged in close proximity to cell processing chamber 120 of fluidics cartridge 110. Counting mechanism 162 can be any mechanism for counting cells in cell processing chamber 120 of fluidics cartridge 110. However, it is a requirement of counting mechanism 162 to be able to distinguish between the cells and the microposts 124 in cell processing chamber 120. Counting mechanism 162 can be based, for example, on electrical resistance (e.g., a Coulter counter), flow cytometry (e.g., a flow cytometer wherein cells flow in a narrow stream in front of a laser beam), image analysis (e.g., an optical imaging system that uses a digital camera and image analysis processes to count the cells), spectrophotometry (e.g., uses an optical density measurement to get an average cell count), and any combinations thereof. In another example, the cells can be labeled and then counted by detecting the label. For example, the cells can be fluorescently tagged and then counted by detecting fluorescence.

Figure 5A:
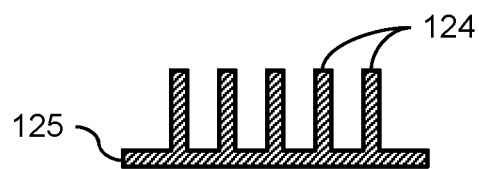
FIG. 5A and FIG. 5B illustrate side views of an example of microposts of the cell processing chamber of the presently disclosed cell processing system.
Figure 5B:
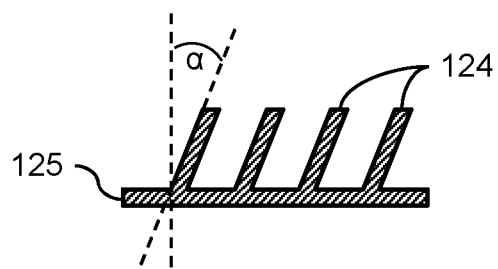

FIG. 5A and FIG. 5B illustrate side views of an example of microposts 124 of micropost array 122 of cell processing chamber 120 of the presently disclosed cell processing system 100. Again, microposts 124 and micropost substrate 125 can be formed, for example, of PDMS. The length, diameter, geometry, orientation, and pitch of microposts 124 in the array can vary. For example, the length of microposts 124 can vary from about 1 μm to about 100 μm. The diameter of microposts 124 can vary from about 0.1 μm to about 10 μm. The cross-sectional shape of microposts 124 can vary. For example, the cross-sectional shape of microposts 124 can circular, ovular, square, rectangular, triangular, and so on. The orientation of microposts 124 can vary. For example, FIG. 5A shows microposts 124 oriented substantially normal to the plane of micropost substrate 125, while FIG. 5B shows microposts 124 oriented at an angle α with respect to normal of the plane of micropost substrate 125. In a neutral position with no deflection force applied, the angle α can be, for example, from about 0 degrees to about 45 degrees.

Figure 6A:
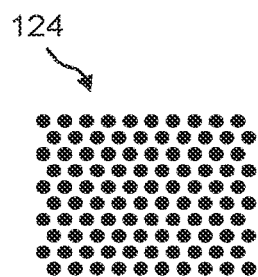
FIG. 6A through FIG. 6E illustrate plan views of examples of micropost arrays.
Figure 6B:
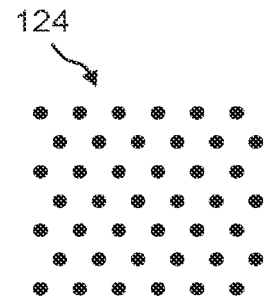
Figure 6C:
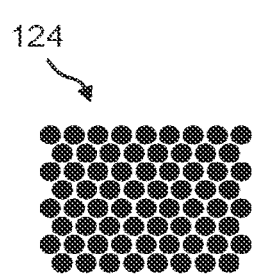
Figure 6D:
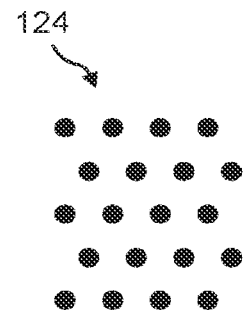
Figure 6E:
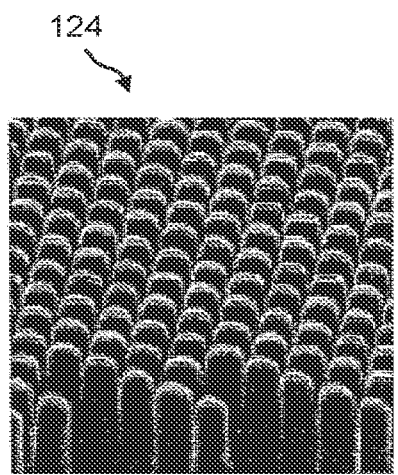

Further, the pitch of microposts 124 within the array can vary, for example, from about 0 μm to about 50 μm. For example, FIG. 6A through FIG. 6D illustrate plan views of examples of configurations of the array of microposts 124. Particularly, FIG. 6A shows an example of microposts 124 that are 0.6 μm in diameter and spaced 1.4 μm apart. FIG. 6B shows an example of microposts 124 that are 0.6 μm in diameter and spaced 2.6 μm apart. FIG. 6C shows an example of microposts 124 that are 1 μm in diameter and spaced 1.5 μm apart. FIG. 6D shows an example of microposts 124 that are 1 μm in diameter and spaced 3 μm apart. It is understood that the size and dimensions depicted in FIG. 6A through FIG. 6D are exemplary only and not limiting. FIG. 6E shows a scanning electron microscope image of an example of an array of microposts 124. Further, FIG. 6A through FIG. 6E show the rows of microposts 124 staggered or offset, which is exemplary only.

Figure 7A:
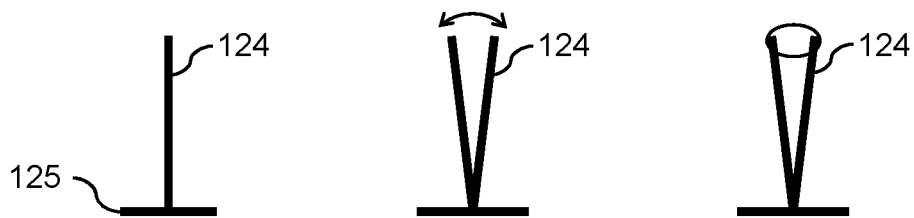
FIG. 7A and FIG. 7B illustrate side views of a micropost and show examples of actuation motion thereof.
Figure 7B:
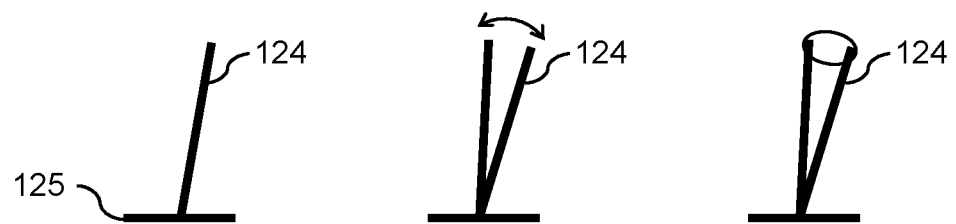

FIG. 7A and FIG. 7B illustrate sides views of a micropost 124 and show examples of actuation motion thereof. Particularly, FIG. 7A shows an example of a micropost 124 oriented substantially normal to the plane of micropost substrate 125. FIG. 7A shows that the distal end of the micropost 124 can move (1) with side-to-side 2D motion only with respect to the fixed proximal end or (2) with circular motion with respect to the fixed proximal end, which is a cone-shaped motion. By contrast, FIG. 7B shows an example of a micropost 124 oriented at an angle with respect to the plane of micropost substrate 125. FIG. 7B shows that the distal end of the micropost 124 can move (1) with tilted side-to-side 2D motion only with respect to the fixed proximal end or (2) with tilted circular motion with respect to the fixed proximal end, which is a tilted cone-shaped motion.

Figure 8A:
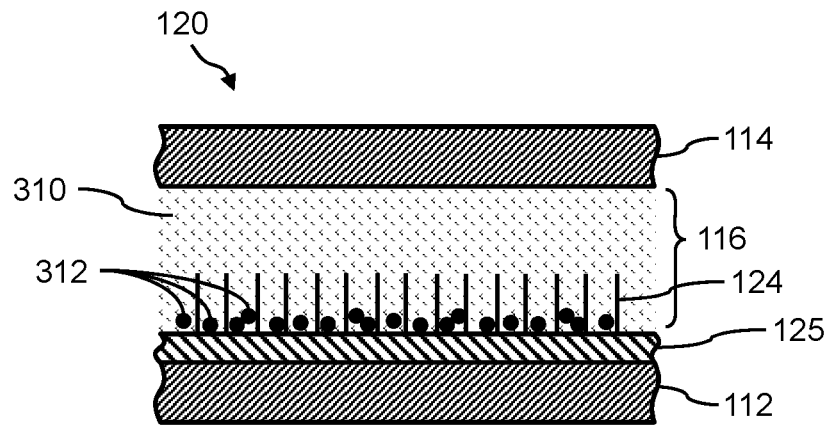
FIG. 8A, FIG. 8B, and FIG. 8C illustrate a side view of the cell processing chamber of the presently disclosed cell processing system and a process of collecting, washing, and recovering cells using the micropost array.
Figure 8B:
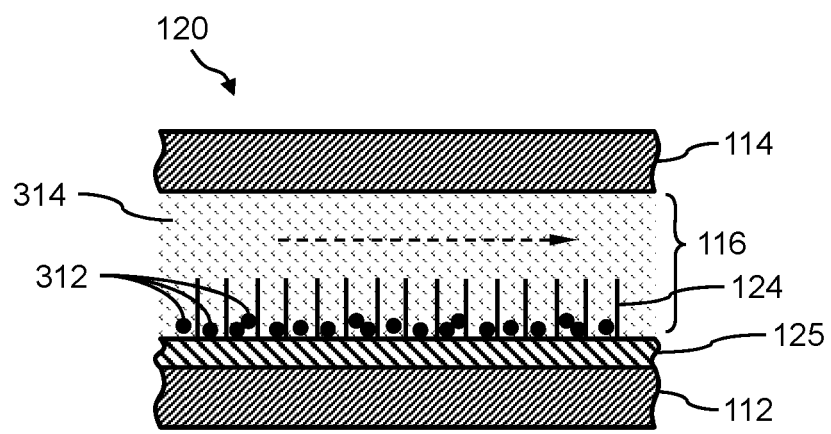
Figure 8C:
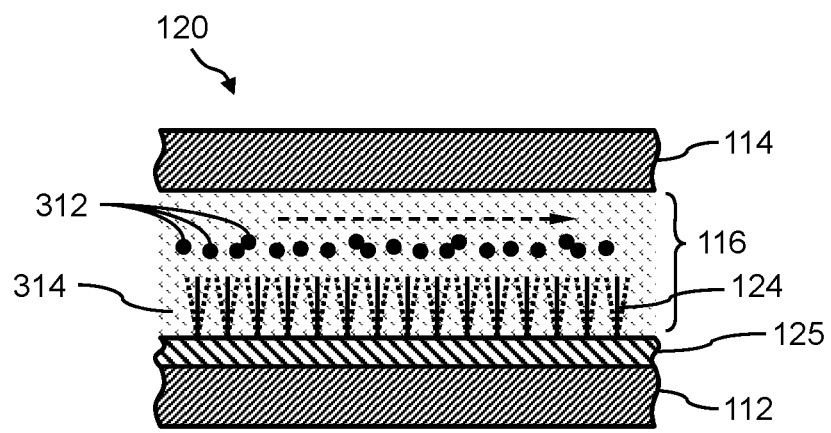

FIG. 8A, FIG. 8B, and FIG. 8C illustrate a side view of cell processing chamber 120 of fluidics cartridge 110 and a process of collecting, washing, and recovering cells using micropost array 122. First and referring now to FIG. 8A, with microposts 124 not actuated, a volume of sample fluid 310 that contains cells 312 is flowed into cell processing chamber 120. Next and referring still to FIG. 8A, with microposts 124 not actuated, cells 312 are allowed to precipitate out by gravity onto the chamber floor (i.e., the micropost substrate) and amongst microposts 124. Next and referring now to FIG. 8B, with microposts 124 not actuated, a cell wash cycle is performed by flowing a wash buffer solution 314 through cell processing chamber 120. Next and referring now to FIG. 8C, a cell recovery cycle is performed by flowing wash buffer solution 314 through cell processing chamber 120 while at the same time actuating microposts 124 in order to resuspend cells 312 into the flow. Particularly, the motion of the actuated microposts 124 kicks cells 312 up and clear of microposts 124 and into the flow of wash buffer solution 314.

FIG. 9 illustrates a block diagram of an example of the presently disclosed cell processing system 100. Again, cell processing system 100 includes cell processing chamber 120 that includes micropost array 122. Also again, cell processing system 100 includes sample reservoir 130, wash reservoir 132, and cell culture media reservoir 133 supplying cell processing chamber 120 and waste reservoir 134 and eluent reservoir 136 at the output of cell processing chamber 120. Also again, actuation mechanism 160 and counting mechanism 162 are provided in close proximity to cell processing chamber 120.

Further, a fluid control port 156 is provided in each of the fluid channels 140. Particularly, a fluid control port 156 is provided at the outlet of sample reservoir 130, another fluid control port 156 is provided at the outlet of wash reservoir 132, another fluid control port 156 is provided at the outlet of cell culture media reservoir 133, another fluid control port 156 is provided at the inlet of waste reservoir 134, and another fluid control port 156 is provided at the inlet of eluent reservoir 136. In one example, the fluid control ports 156 are pinch valves.

Additionally, a pump 164 is fluidly connected to sample reservoir 130, a pump 166 is fluidly connected to wash reservoir 132, and a pump 167 is fluidly connected to cell culture media reservoir 133. Pumps 164, 166, and 167 can be, for example, small manual or electric pumps (e.g., syringe pumps) that can supply positive and/or negative pressure to cell processing chamber 120.

Cell processing system 100 also includes a controller 168 for controlling the overall operations of cell processing system 100. For example, controller 168 can be used to control the operations of fluid control ports 156, actuation mechanism 160, counting mechanism 162, pump 164, and pump 166. Controller 168 can be any computing device, controller, and/or microcontroller that is capable of executing program instructions. Further, data storage (not shown) can be associated with controller 168.

Further, cell processing system 100 can have a user interface (UI) 170. UI 170 can include, for example, any number and types of switches, pushbuttons, visual indicators (e.g., light-emitting diodes (LEDs)), audible indicators (e.g., beeps, buzzes), tactile indicators (i.e., vibration), and the like. For example, FIG. 1 and FIG. 2 show a power pushbutton 172 on control instrument 150.

Optionally, cell processing system 100 can include a communications interface 174. Communications interface 174 can be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, cellular networks, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. In one example, communications interface 174 can be used to communicate device health information, such as the battery status, or cell processing status. In another example, communications interface 174 can be used to communicate with a desktop computer application (not shown) or mobile app (not shown) associated with cell processing system 100.

Further, a power source 180 is provided for powering all of the active components of cell processing system 100. In one example, power source 180 can be any rechargeable or non-rechargeable batteries. In another example, power source 180 can be an AC adaptor that converts standard AC power to a DC voltage.

Under the control of controller 168, various process cycles can be performed using cell processing system 100 as follows.

SAMPLE LOADING CYCLE (or cell collection cycle)—to load cell processing chamber 120 with sample fluid, fluid control ports 156 of wash reservoir 132, cell culture media reservoir 133, waste reservoir 134, and eluent reservoir 136 are closed; fluid control port 156 of sample reservoir 130 is opened; pump 164 is activated, pump 166 and pump 167 are not activated, actuation mechanism 160 is not activated, and counting mechanism 162 is not activated.

CELL WASH CYCLE—to wash the cells in processing chamber 120, fluid control ports 156 of sample reservoir 130, cell culture media reservoir 133, and eluent reservoir 136 are closed; fluid control ports 156 of wash reservoir 132 and waste reservoir 134 are opened; pump 164 and pump 167 are not activated, pump 166 is activated, actuation mechanism 160 is not activated, and counting mechanism 162 is not activated.

CELL CULTURE CYCLE—to culture the cells in processing chamber 120, fluid control ports 156 of sample reservoir 130, wash reservoir 132, and eluent reservoir 136 are closed; fluid control ports 156 of cell culture media reservoir 133 and waste reservoir 134 are opened; pump 164 and pump 166 are not activated, pump 167 is activated, actuation mechanism 160 is not activated, and counting mechanism 162 is not activated.

CELL COUNTING CYCLE—to count the cells in processing chamber 120, fluid control ports 156 of sample reservoir 130, wash reservoir 132, cell culture media reservoir 133, waste reservoir 134, and eluent reservoir 136 are closed; pump 164 is not activated, pump 166 is not activated, pump 167 is not activated, actuation mechanism 160 is not activated, and counting mechanism 162 is activated.

CELL RECOVERY CYCLE—to recover the cells from processing chamber 120, fluid control ports 156 of sample reservoir 130, cell culture media reservoir 133, and waste reservoir 134 are closed; fluid control ports 156 of wash reservoir 132 and eluent reservoir 136 are opened; pump 164 and pump 167 are not activated, pump 166 is activated, actuation mechanism 160 is activated, and counting mechanism 162 is not activated.

Cell processing system 100 is not limited to a sample loading cycle, a cell wash cycle, a cell counting cycle, a cell culture cycle, and/or a cell recovery cycle. These cycles are exemplary only. Cell processing system 100 can be used to perform other cell processing cycles, such as, but not limited to, a sample loading or cell collection cycle, a cell wash cycle, a cell counting cycle, a cell recovery cycle, a cell concentration cycle, a cell filtration cycle, a cell lysis cycle, a cell de-clumping cycle, and the like.

Figure 10:
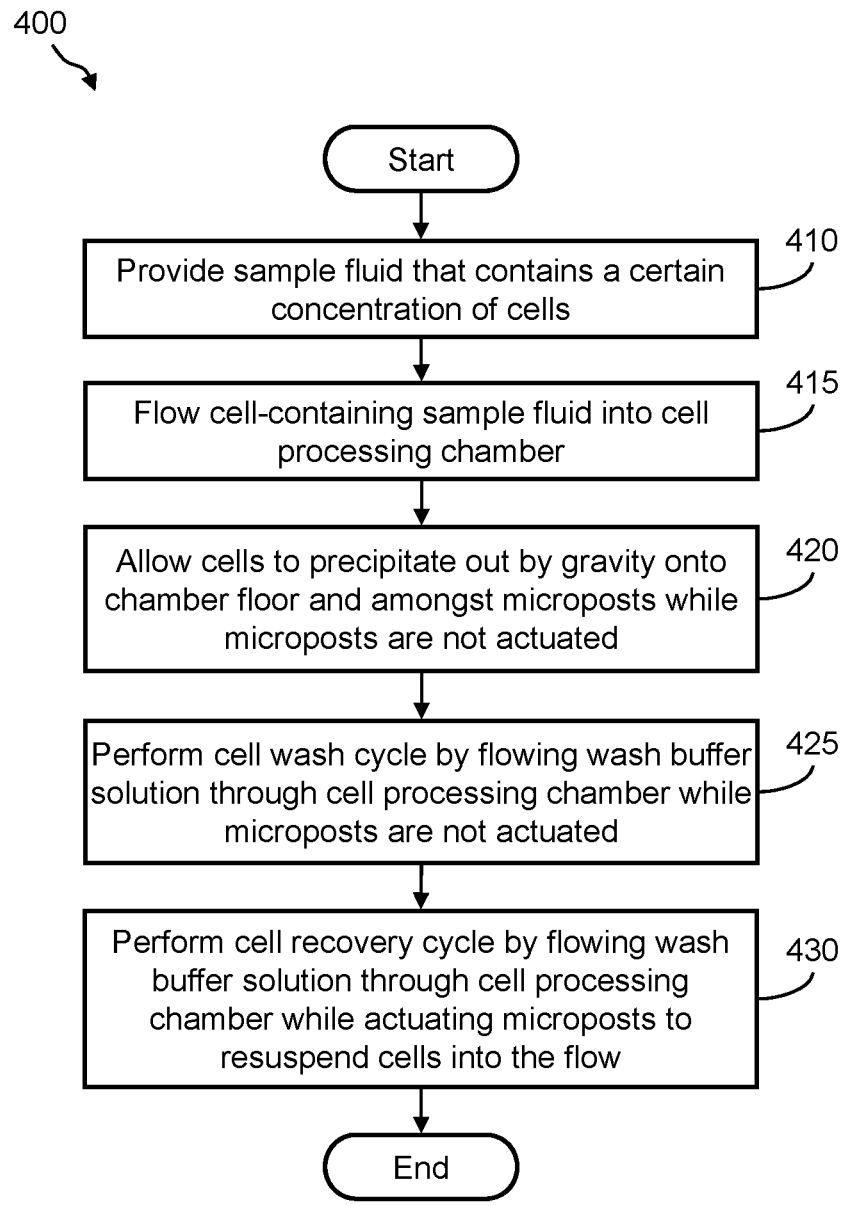
FIG. 10 illustrates a flow diagram of an example of a method of using the presently disclosed cell processing system to collect, wash, and recover cells.

FIG. 10 illustrates a flow diagram of an example of a method 400 of using the presently disclosed cell processing system 100 to collect, wash, and recover cells. Method 400 may include, but is not limited to, the following steps.

At a step 410, a sample fluid is provided that contains a certain concentration of cells. In one example, sample reservoir 130 is a 200 μL reservoir that is holding a 200 μL-sample produced using a centrifugation process. For example, previous to cell processing system 100, a 10 mL sample undergoes a cell concentration process by centrifugation to produce a cell pellet. Then, the cell pellet is resuspended into a 200 μL solution, which is then supplied to sample reservoir 130 of cell processing system 100. The concentration of this 200 μL-sample can be, for example, from about 1 cells/uL to about 10,000 cells/uL.

At a step 415, the cell-containing sample fluid is flowed into cell processing chamber 120. For example and referring again to FIG. 8A, with microposts 124 not actuated, a volume of sample fluid 310 that contains cells 312 is flowed out of sample reservoir 130 and fills cell processing chamber 120.

At a step 420, the cells are allowed time to precipitate out by gravity, microfluidic cell separator (e.g., see FIG. 16A and FIG. 16B), and/or dielectrophoresis (e.g., see FIG. 17) onto the chamber floor (i.e., the micropost substrate) and amongst microposts 124 while microposts 124 are not actuated. For example and referring again to FIG. 8A, with microposts 124 not actuated, cells 312 are allowed time to precipitate out by gravity onto the floor of cell processing chamber 120 and collect amongst microposts 124. In one example, the time allowed is from about 1 minute to about 2 minutes.

At a step 425, a cell wash cycle is performed by flowing wash buffer solution through cell processing chamber 120 while microposts 124 are not actuated. For example and referring again to FIG. 8B, with microposts 124 not actuated, a cell wash cycle is performed by flowing a volume of wash buffer solution 314 out of wash reservoir 132, flushing through cell processing chamber 120, and then collected in waste reservoir 134. All the while, cells 312 are trapped amongst microposts 124 of micropost array 122 and thereby held inside cell processing chamber 120. This step can be repeated any number of times until the cells are suitably cleaned.

At a step 430, a cell recovery cycle is performed by flowing wash buffer solution through cell processing chamber 120 while actuating microposts 124 to resuspend the cells into the flow. For example and referring again to FIG. 8C, a cell recovery cycle is performed by flowing wash buffer solution 314 through cell processing chamber 120 while at the same time actuating microposts 124 (via actuation mechanism 160) in order to resuspend cells 312 into the flow. Particularly, the motion of the actuated microposts 124 kicks cells 312 up and clear of microposts 124 and into the flow of wash buffer solution 314. The resulting cell-containing eluent flows out of cell processing chamber 120 and is collected in eluent reservoir 136.

Figure 11:
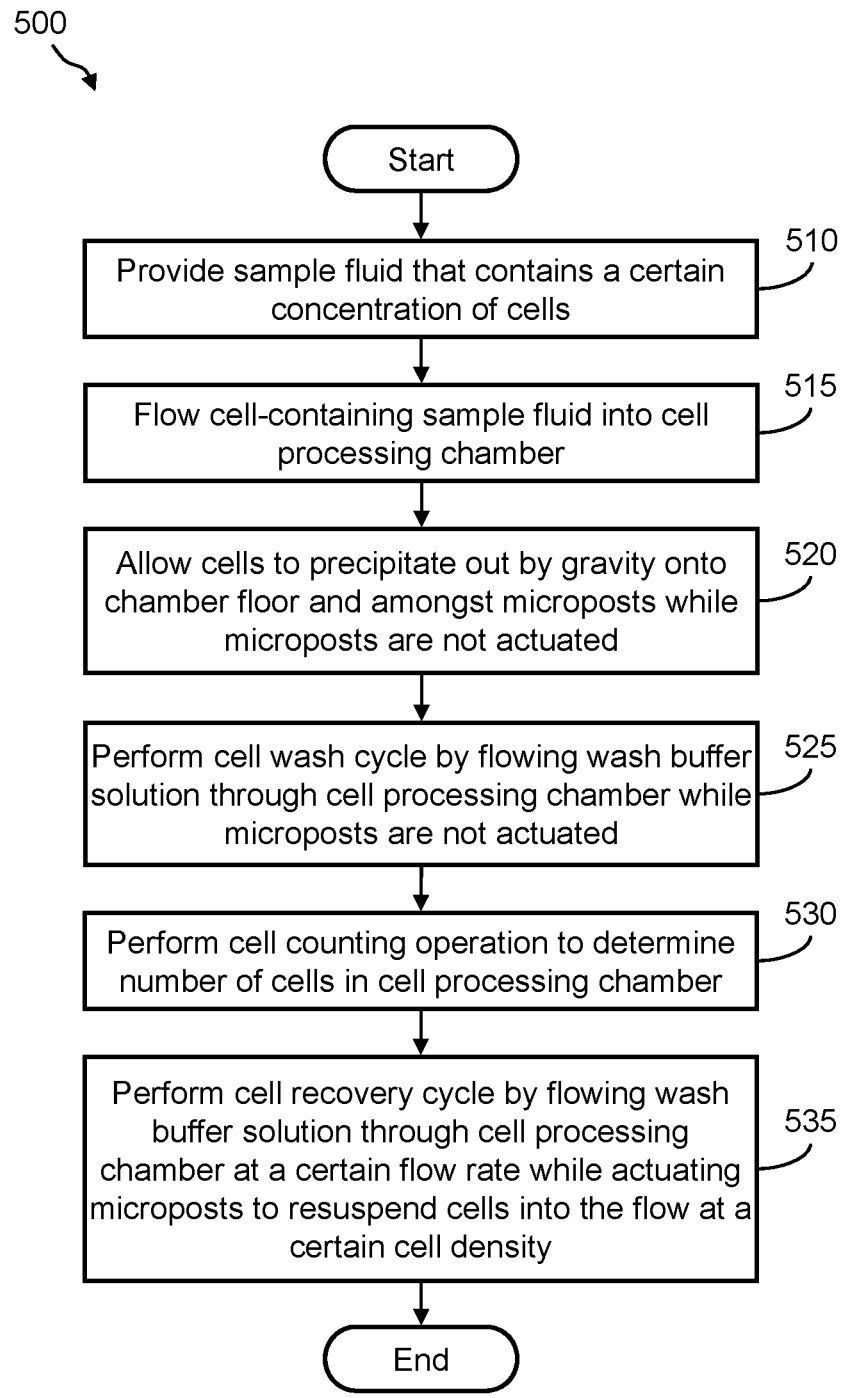
FIG. 11 illustrates a flow diagram of an example of a method of using the presently disclosed cell processing system to collect, wash, count, and recover cells as a predetermined density.

FIG. 11 illustrates a flow diagram of an example of a method 500 of using the presently disclosed cell processing system 100 to collect, wash, count, and recover cells at a predetermined cell density. Method 500 may include, but is not limited to, the following steps.

At a step 510, a sample fluid is provided that contains a certain concentration of cells. In one example, sample reservoir 130 is a 200 μL reservoir that is holding a 200 μL-sample produced using a centrifugation process. For example, previous to cell processing system 100, a 10 mL sample undergoes a cell concentration process by centrifugation to produce a cell pellet. Then, the cell pellet is resuspended into a 200 μL solution, which is then supplied to sample reservoir 130 of cell processing system 100. The concentration of this 200 μL-sample can be, for example, from about 1 cells/uL to about 10,000 cells/uL.

At a step 515, the cell-containing sample fluid is flowed into cell processing chamber 120. For example and referring again to FIG. 8A, with microposts 124 not actuated, a volume of sample fluid 310 that contains cells 312 is flowed out of sample reservoir 130 and fills cell processing chamber 120.

At a step 520, the cells are allowed time to precipitate out by gravity onto the chamber floor (i.e., the micropost substrate) and amongst microposts 124 while microposts 124 are not actuated. For example and referring again to FIG. 8A, with microposts 124 not actuated, cells 312 are allowed time to precipitate out by gravity onto the floor of cell processing chamber 120 and collect amongst microposts 124. In one example, the time allowed is from about 1 minute to about 2 minutes.

At a step 525, a cell wash cycle is performed by flowing wash buffer solution through cell processing chamber 120 while microposts 124 are not actuated. For example and referring again to FIG. 8B, with microposts 124 not actuated, a cell wash cycle is performed by flowing a volume of wash buffer solution 314 out of wash reservoir 132, flushing through cell processing chamber 120, and then collected in waste reservoir 134. All the while, cells 312 are trapped amongst microposts 124 of micropost array 122 and thereby held inside cell processing chamber 120. This step can be repeated any number of times until the cells are suitably cleaned.

At a step 530, a cell counting operation is performed to determine the number of cells in cell processing chamber 120. For example, while microposts 124 are not actuated and while cells 312 are resting on the floor of cell processing chamber 120, counting mechanism 162 is activated to determine the number of cells 312 in cell processing chamber 120. In one example, counting mechanism 162 is an optical imaging system that uses a digital camera and image analysis processes to count the cells 312.

At a step 535, a cell recovery cycle is performed by flowing wash buffer solution through cell processing chamber 120 at a certain flow rate and while actuating microposts 124 to resuspend the cells into the flow at a certain cell density. For example and referring again to FIG. 8C, a cell recovery cycle is performed by flowing wash buffer solution 314 through cell processing chamber 120 at a certain flow rate and while at the same time actuating microposts 124 (via actuation mechanism 160) in order to resuspend cells 312 into the flow at a certain cell density (e.g., 15 cells/uL). Particularly, the motion of the actuated microposts 124 kicks cells 312 up and clear of microposts 124 and into the flow of wash buffer solution 314. The resulting cell-containing eluent at the desired cell density (e.g., 15 cells/uL) flows out of cell processing chamber 120 and is collected in eluent reservoir 136. The contents of eluent reservoir 136 is now available for downstream processes, such as in an automated robotics system (e.g., the Tecan robotic system used for sample prep). In this step, the dispensed cell density can be specified with some tolerance, such as 15 cells/uL ±2 or ±5, and so on.

Referring now again to FIG. 1 through FIG. 11, cell processing system 100 that includes fluidics cartridge 110 and control instrument 150 and methods 400, 500 are well-suited for the sample preparation process. Particularly, cell processing system 100 and methods 400, 500 provide ways of processing cells that (1) do not involve binding and (2) rely on fluidics. Examples of processes that can be performed using the presently disclosed cell processing system 100 and methods 400, 500 include, but are not limited to, cell concentration, cell collection, cell filtration, cell washing, cell counting, cell recovery, cell lysis, cell de-clumping, and the like. In one example, actuating microposts 124 in cell processing chamber 120 can be used to create a beating motion for cell lysis. In another example, if clumps of cells are present (e.g., sticky cells), microposts 124 can be actuated to create an agitation or beating motion to break up the clumps. One purpose is to break up the clumps before cells precipitate out amongst the microposts 124 to be counted.

Further, in other configurations, a microarray is provided on the opposing surface to the microposts. The cells are captured amongst the microposts 124 in the chamber, then a lysis buffer is flushed into the chamber to burst the cells on-cartridge, then the microposts are actuated to mix everything up and drive the cells to the microarray, and then perform detection. In this example, the cell recovery step is omitted.

Figure 12:
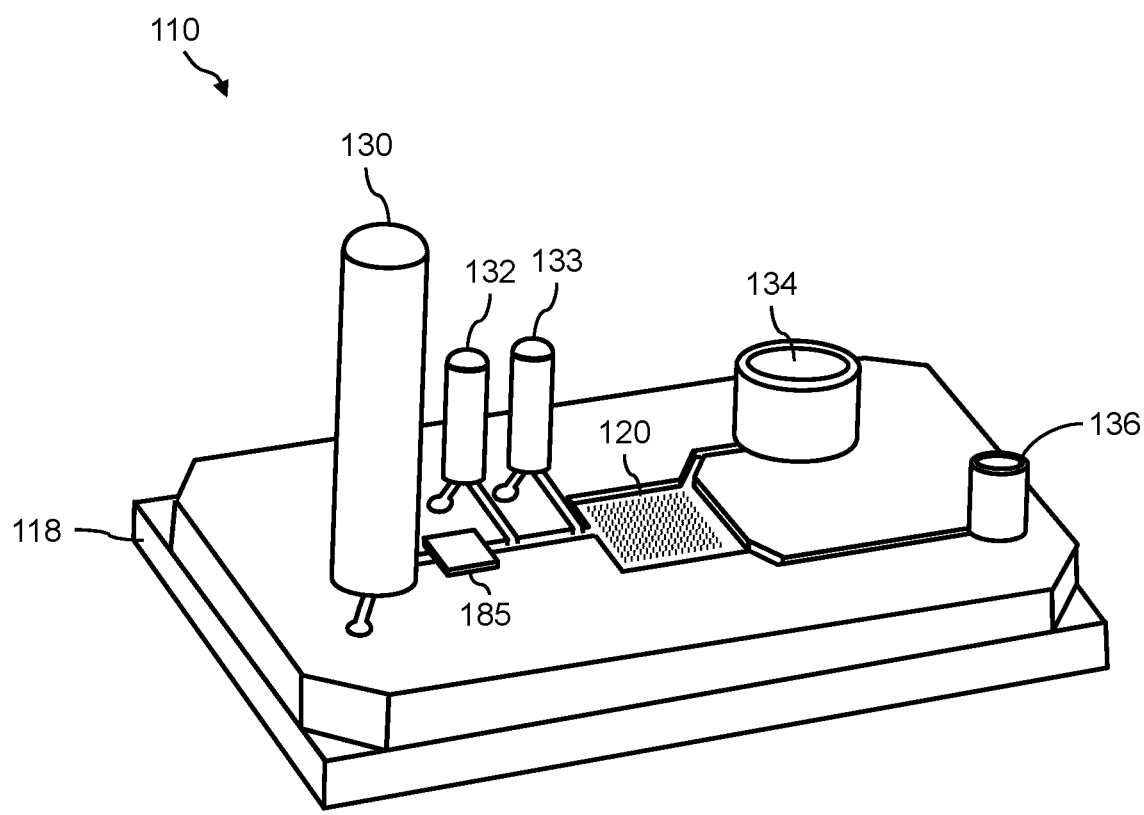
FIG. 12 illustrates a perspective view of an example of the fluidics cartridge of the presently disclosed cell processing system that further includes a cell concentration module.

FIG. 12 illustrates a perspective view of an example of fluidics cartridge 110 of the presently disclosed cell processing system 100 that further includes a cell concentration module 185 (not drawn to scale). For example, cell concentration module 185 is an onboard concentration module that can be used, for example, to perform the cell concentration process of the original sample that is typically done by centrifugation to produce the highly concentrated 200 μL-sample, as described, for example, in step 410 of method 400 of FIG. 10 and step 510 of method 500 of FIG. 11. Accordingly, in this example, sample reservoir 130 can be a 10 mL reservoir holding the original 10 mL-sample, which is then supplied to cell concentration module 185. Then, using microfluidics, cell concentration module 185 in fluidics cartridge 110 is used to perform a cell concentration process to produce a cell concentration that is substantially equivalent to the 200 μL-sample that is conventionally produced by centrifugation. In this way, cell concentration module 185 can be used to replace the conventional centrifugation process.

Figure 13:
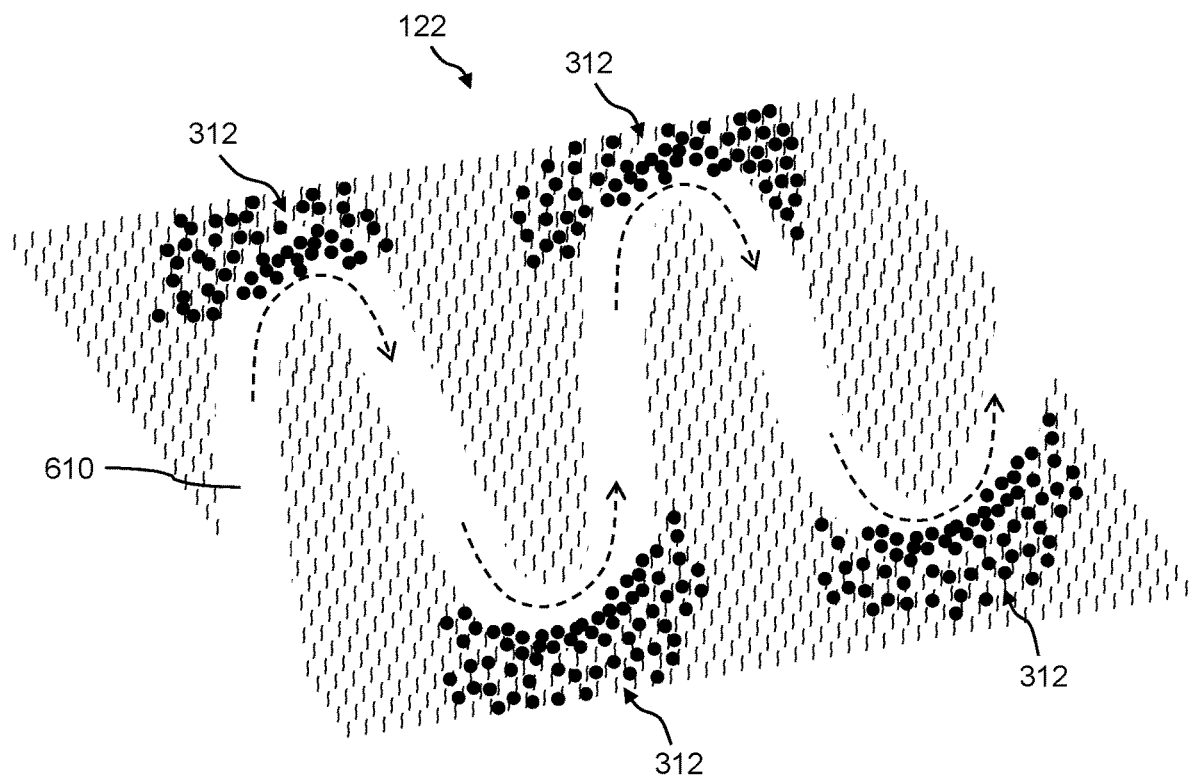
FIG. 13 and FIG. 14 show plan views of examples of flow paths formed in the micropost array, wherein the flow paths are designed to collect cells.
Figure 14:
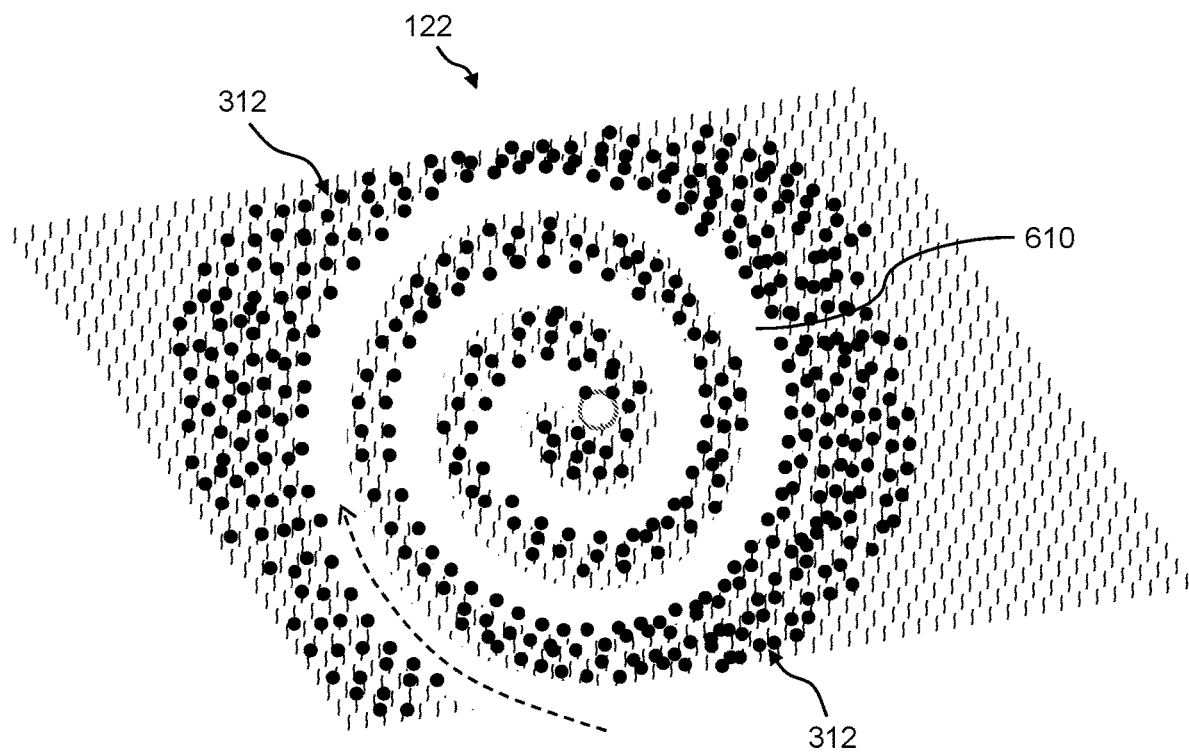

FIG. 13 and FIG. 14 show plan views of examples of flow paths 610 formed in micropost array 122 that are designed to collect cells. A flow path 610 can be formed by the absence of microposts 124 in micropost array 122 and wherein at least some portion of the flow path 610 is curved. For example, FIG. 13 shows a serpentine-shaped flow path 610, wherein cells 312 in the flow tend to aggregate at the outside of the curves of the serpentine-shaped flow path 610, and consequently get pushed into the microposts 124 that define the soft wall of the path. Once among the field of microposts 124, the fluid flow rate will drop, and the cells will precipitate to the bottom of the channel. Similarly, FIG. 14 shows a spiral-shaped flow path 610, wherein cells 312 in the flow tend to aggregate at the outside of the continuous curve of the spiral-shaped flow path 610 and consequently get pushed into the microposts 124.

Figure 15A:
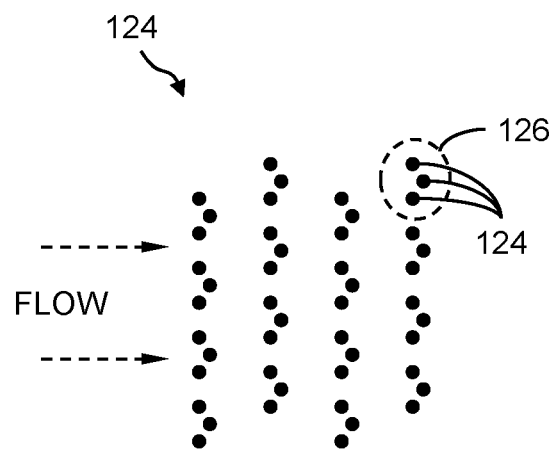
FIG. 15A and FIG. 15B illustrate plan views of example micropost configurations for trapping cells.
Figure 15B:
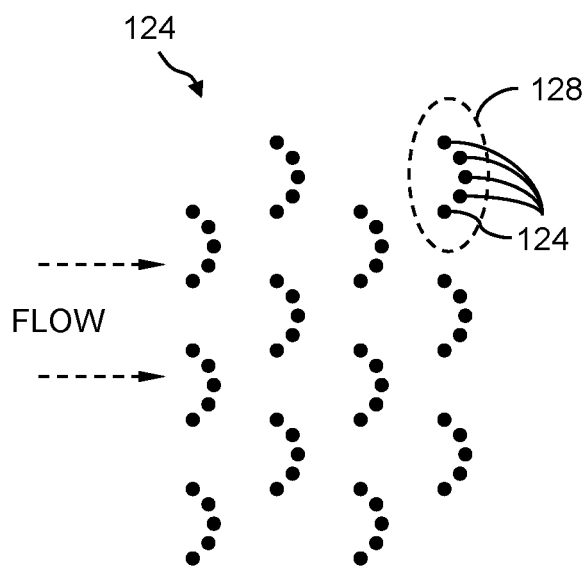

FIG. 15A and FIG. 15B illustrate plan views of example micropost configurations for trapping cells. Particularly, FIG. 15A shows a micropost-arc 126 that is formed of an arrangement of three microposts 124. Similarly, FIG. 15B shows a micropost-arc 128 that is formed of an arrangement of five microposts 124. Micropost-arc 126 and micropost-arc 128 are examples of physical barriers against which cells can collide and be trapped. In a subsequent step, the cells can be released by actuating microposts 124, as described, for example, in step 430 of method 400 of FIG. 10 and step 535 of method 500 of FIG. 11. The micropost barriers are not limited to arc-shaped. The micropost barriers can be any shape, such as, but not limited to, arc-shaped, U-shaped, V-shaped, bar-shaped, and the like.

The serpentine-shaped flow path 610 shown in FIG. 13, the spiral-shaped flow path 610 shown in FIG. 14, and the arc-shaped micropost configurations shown in FIG. 15A and FIG. 15B are examples of patterning microposts 124 in ways to collect, trap, and/or catch cells that can be used in place of or in combination with precipitating out cells by gravity. In one example, the method of patterning microposts 124 can be to fabricate microposts 124 in a very high density array and then use a tool, such as an embossing tool, to crush the unwanted microposts 124 and create the negative space leaving the desired micropost shapes behind.

Figure 16A:
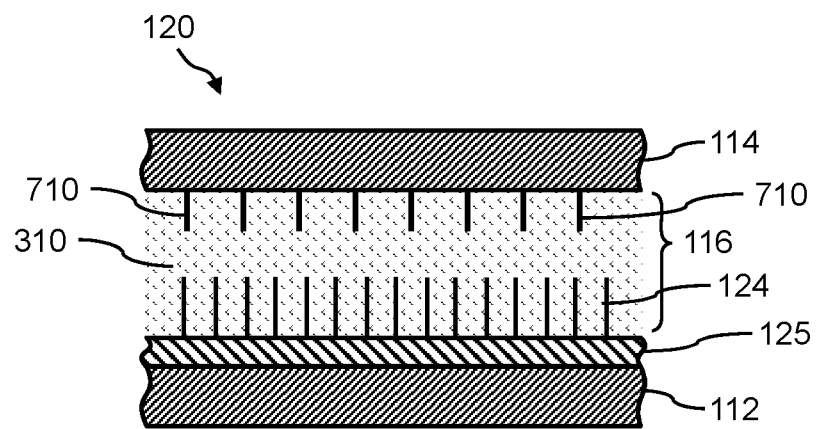
FIG. 16A and FIG. 16B show a configuration of the cell processing chamber that includes features for assisting cells to precipitate out of solution.
Figure 16B:
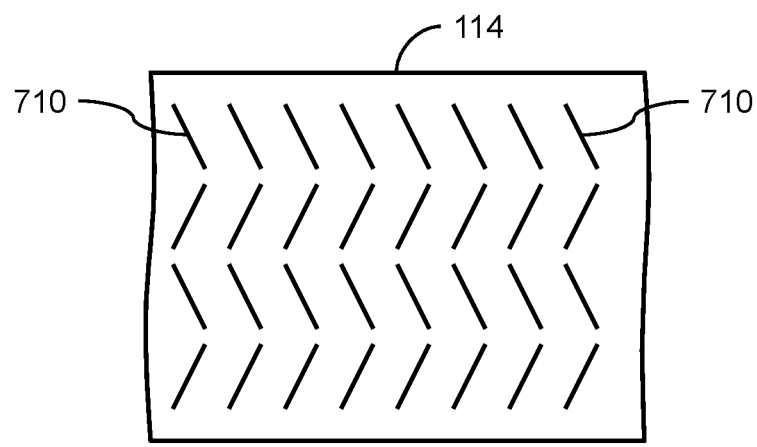

FIG. 16A and FIG. 16B show a configuration of cell processing chamber 120 that includes features for assisting cells to precipitate out of solution. FIG. 16A is a side view of cell processing chamber 120. FIG. 16B is a plan view of top substrate 114 of cell processing chamber 120. In this example, a set of features 710 is provided in, for example, a herringbone configuration patterned on top substrate 114 as shown in FIG. 16B, which is the surface opposite micropost array 122. Because of the presence of features 710, cell processing chamber 120 can provide the added function of microfluidic cell separation. Particularly, once cells are trapped against features 710, the fluid flow rate will drop, and the cells will precipitate to the bottom of cell processing chamber 120.

Figure 17:
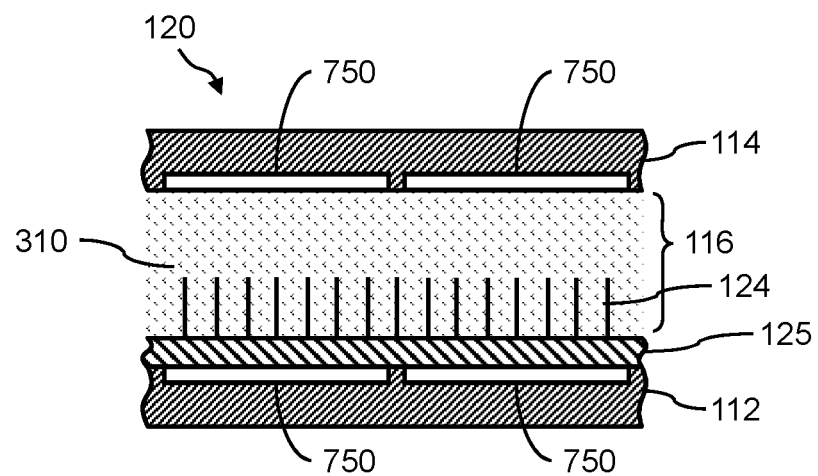
FIG. 17 shows another configuration of the cell processing chamber that includes features for assisting cells to precipitate out of solution.

FIG. 17 shows another configuration of cell processing chamber 120 that includes features for assisting cells to precipitate out of solution. In this example, one or more electrodes 750 (e.g., electrowetting electrodes) can be provided in bottom substrate 112, top substrate 114, or both bottom substrate 112 and top substrate 114. Because of the presence of electrodes 750, cell processing chamber 120 can provide the added function of dielectrophoresis.

Figure 18:
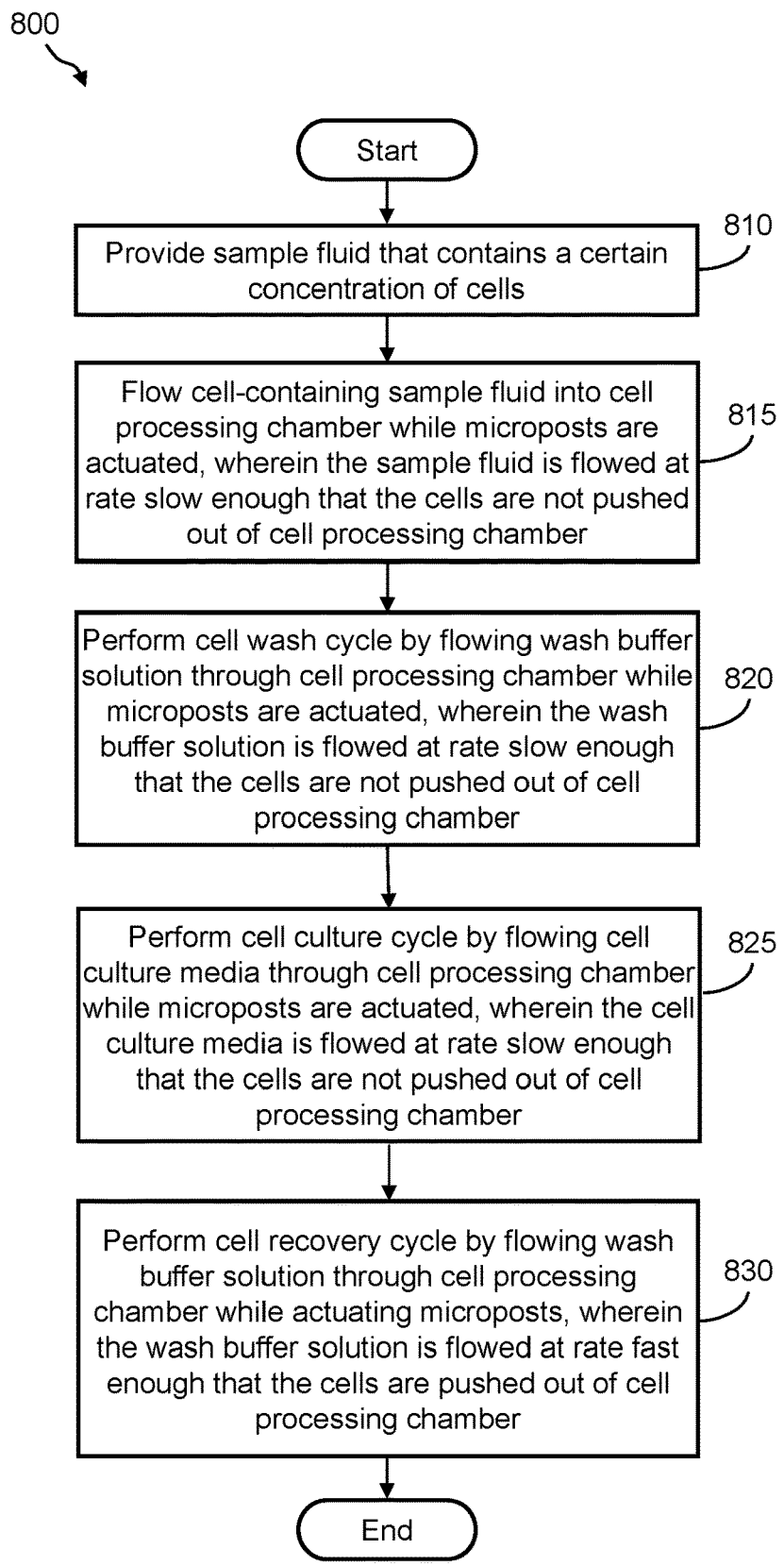
FIG. 18 illustrates a flow diagram of an example of another method of using the presently disclosed cell processing system to collect, wash, and recover cells.

FIG. 18 illustrates a flow diagram of an example of a method 800 of using the presently disclosed cell processing system 100 to collect, wash, and recover cells. Method 800 may include, but is not limited to, the following steps.

At a step 810, a sample fluid is provided that contains a certain concentration of cells. In one example, sample reservoir 130 is a 200 μL reservoir that is holding a 200 μL-sample produced using a centrifugation process. For example, previous to cell processing system 100, a 10 mL sample undergoes a cell concentration process by centrifugation to produce a cell pellet. Then, the cell pellet is resuspended into a 200 μL solution, which is then supplied to sample reservoir 130 of cell processing system 100. The concentration of this 200 μL-sample can be, for example, from about 1 cells/uL to about 10,000 cells/uL.

At a step 815, the cell-containing sample fluid is flowed into cell processing chamber 120 while microposts 124 are actuated, wherein the sample fluid is flowed at rate slow enough that the cells are not pushed out of cell processing chamber 120. For example, with microposts 124 actuated, a volume of sample fluid 310 that contains cells 312 is flowed out of sample reservoir 130 and fills cell processing chamber 120, wherein the sample fluid is flowed at a rate slow enough that the cells are not pushed out of cell processing chamber 120. Particularly, the motion of the actuated microposts 124 acts as an impeller to keep the cells suspended in cell processing chamber 120.

At a step 820, a cell wash cycle is performed by flowing wash buffer solution through cell processing chamber 120 while microposts 124 are actuated, wherein the wash buffer solution is flowed at rate slow enough that the cells are not pushed out of cell processing chamber 120. For example, with microposts 124 actuated, a cell wash cycle is performed by flowing a volume of wash buffer solution 314 out of wash reservoir 132, flushing through cell processing chamber 120, and then collected in waste reservoir 134, wherein the wash buffer solution is flowed at a rate slow enough that the cells are not pushed out of cell processing chamber 120. Particularly, the motion of the actuated microposts 124 acts as an impeller to keep the cells suspended in cell processing chamber 120.

At a step 825, a cell culture cycle is performed by flowing cell culture media through cell processing chamber 120 while microposts 124 are actuated, wherein the cell culture media is flowed at rate slow enough that the cells are not pushed out of cell processing chamber 120. For example, with microposts 124 actuated, a cell culture cycle is performed by flowing a volume of cell culture media out of cell culture media reservoir 133, filling cell processing chamber 120, wherein the wash buffer solution is flowed at a rate slow enough that the cells are not pushed out of cell processing chamber 120. Particularly, the motion of the actuated microposts 124 acts as an impeller to keep the cells suspended in cell processing chamber 120.

At a step 830, a cell recovery cycle is performed by flowing wash buffer solution through cell processing chamber 120 while actuating microposts 124, wherein the wash buffer solution is flowed at rate fast enough that the cells are pushed out of cell processing chamber 120. For example, a cell recovery cycle is performed by flowing wash buffer solution 314 through cell processing chamber 120 while at the same time actuating microposts 124 (via actuation mechanism 160), wherein the wash buffer solution is flowed at rate fast enough that the cells are pushed out of cell processing chamber 120. The resulting cell-containing eluent flows out of cell processing chamber 120 and is collected in eluent reservoir 136.

Figure 19:
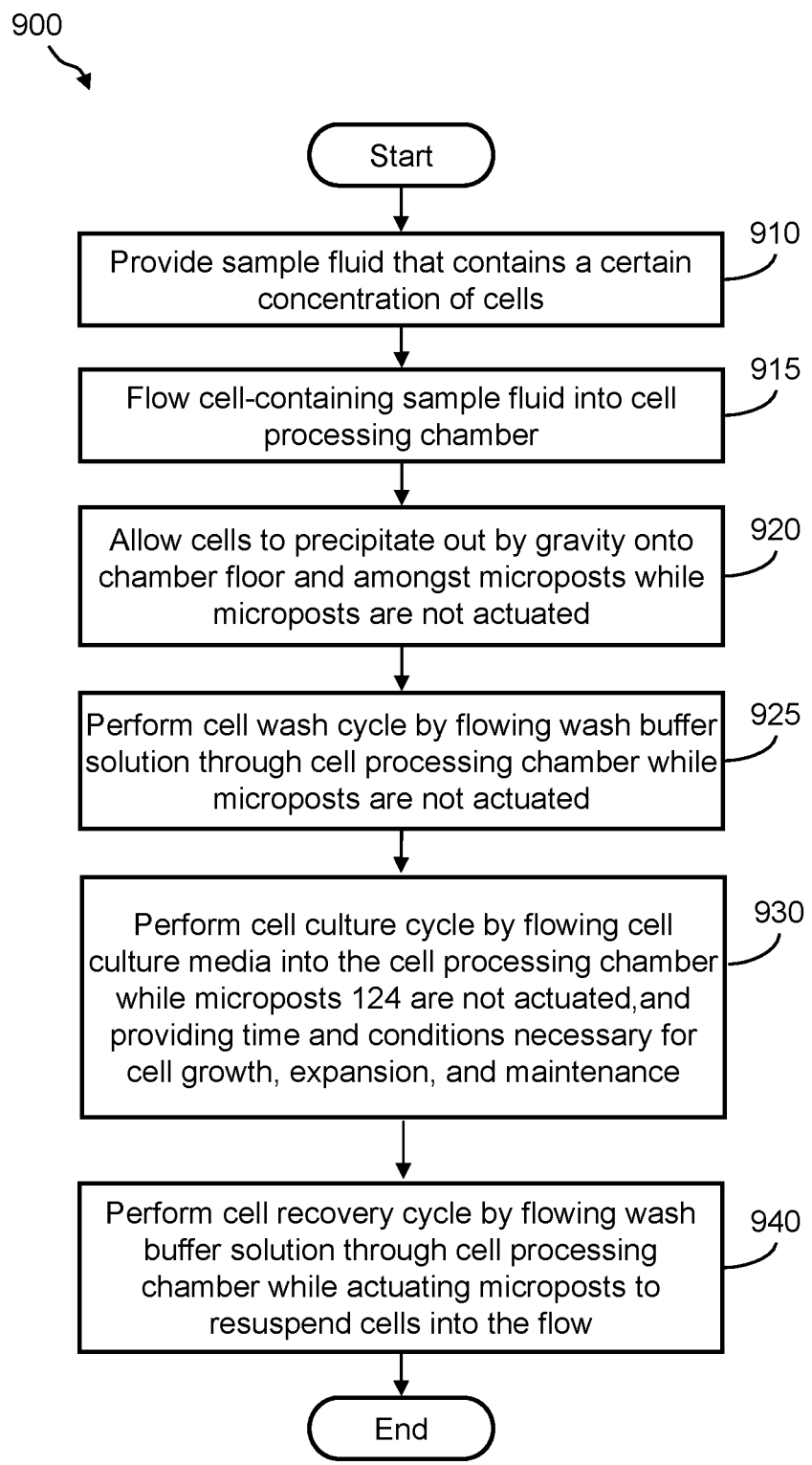
FIG. 19 illustrates a flow diagram of an example of a method of using the presently disclosed cell processing system to collect, wash, culture, and recover cells.

FIG. 19 illustrates a flow diagram of an example of a method 900 of using the presently disclosed cell processing system 100 to collect, wash, culture, and recover cells. Method 900 may include, but is not limited to, the following steps.

At a step 910, a sample fluid is provided that contains a certain concentration of cells. In one example, sample reservoir 130 is a 200 µL reservoir that is holding a 200 µL-sample produced using a centrifugation process. For example, previous to cell processing system 100, a 10 mL sample undergoes a cell concentration process by centrifugation to produce a cell pellet. Then, the cell pellet is resuspended into a 200 µL solution, which is then supplied to sample reservoir 130 of cell processing system 100. The concentration of this 200 µL-sample can be, for example, from about 1 cells/uL to about 10,000 cells/uL.

At a step 915, the cell-containing sample fluid is flowed into cell processing chamber 120. For example and referring again to FIG. 8A, with microposts 124 not actuated, a volume of sample fluid 310 that contains cells 312 is flowed out of sample reservoir 130 and fills cell processing chamber 120.

At a step 920, the cells are allowed time to precipitate out by gravity, microfluidic cell separator (e.g., see FIG. 16A and FIG. 16B), and/or dielectrophoresis (e.g., see FIG. 17) onto the chamber floor (i.e., the micropost substrate) and amongst microposts 124 while microposts 124 are not actuated. For example and referring again to FIG. 8A, with microposts 124 not actuated, cells 312 are allowed time to precipitate out by gravity onto the floor of cell processing chamber 120 and collect amongst microposts 124. In one example, the time allowed is from about 1 minute to about 2 minutes.

At a step 925, a cell wash cycle is performed by flowing wash buffer solution through cell processing chamber 120 while microposts 124 are not actuated. For example and referring again to FIG. 8B, with microposts 124 not actuated, a cell wash cycle is performed by flowing a volume of wash buffer solution 314 out of wash reservoir 132, flushing through cell processing chamber 120, and then collected in waste reservoir 134. All the while, cells 312 are trapped amongst microposts 124 of micropost array 122 and thereby held inside cell processing chamber 120. This step can be repeated any number of times until the cells are suitably cleaned.

At step 930, a cell culture cycle is performed by flowing cell culture media into cell processing chamber 120 while microposts 124 are not actuated and providing time and conditions necessary for cell growth, expansion, and maintenance.

At a step 940, a cell recovery cycle is performed by flowing wash buffer solution through cell processing chamber 120 while actuating microposts 124 to resuspend the cells into the flow. For example and referring again to FIG. 8C, a cell recovery cycle is performed by flowing wash buffer solution 314 through cell processing chamber 120 while at the same time actuating microposts 124 (via actuation mechanism 160) in order to resuspend cells 312 into the flow. Particularly, the motion of the actuated microposts 124 kicks cells 312 up and clear of microposts 124 and into the flow of wash buffer solution 314. The resulting cell-containing eluent flows out of cell processing chamber 120 and is collected in eluent reservoir 136.

Figure 20:
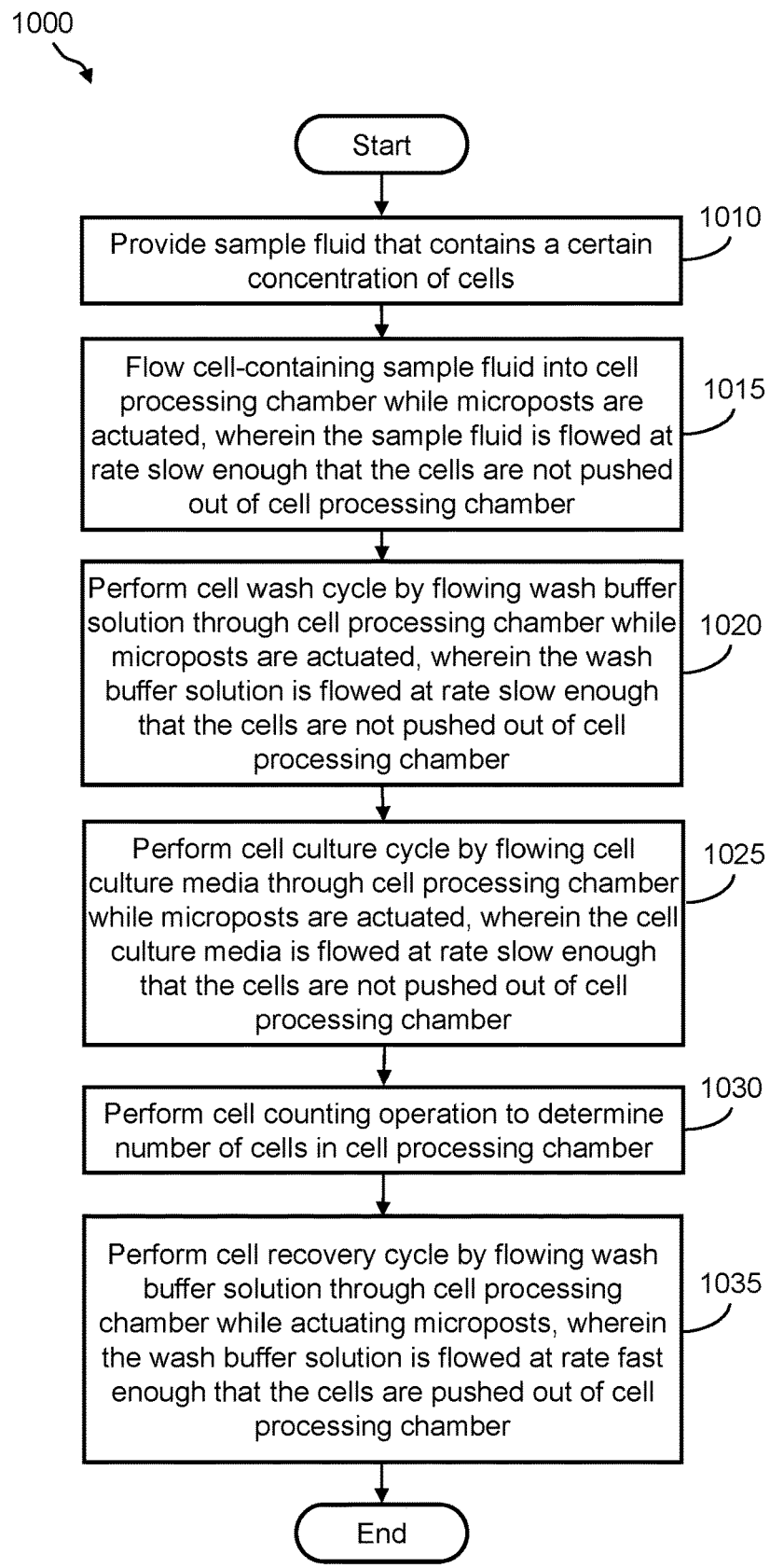
FIG. 20 illustrates a flow diagram of an example of a method of using the presently disclosed cell processing system to collect, wash, culture, count, and recover cells.

FIG. 20 illustrates a flow diagram of an example of a method 1000 of using the presently disclosed cell processing system 100 to collect, wash, count, and recover cells. Method 1000 may include, but is not limited to, the following steps.

At a step 1010, a sample fluid is provided that contains a certain concentration of cells. In one example, sample reservoir 130 is a 200 µL reservoir that is holding a 200 µL-sample produced using a centrifugation process. For example, previous to cell processing system 100, a 10 mL sample undergoes a cell concentration process by centrifugation to produce a cell pellet. Then, the cell pellet is resuspended into a 200 µL solution, which is then supplied to sample reservoir 130 of cell processing system 100. The concentration of this 200 µL-sample can be, for example, from about 1 cells/uL to about 10,000 cells/uL.

At a step 1015, the cell-containing sample fluid is flowed into cell processing chamber 120 while microposts 124 are actuated, wherein the sample fluid is flowed at rate slow enough that the cells are not pushed out of cell processing chamber 120. For example, with microposts 124 actuated, a volume of sample fluid 310 that contains cells 312 is flowed out of sample reservoir 130 and fills cell processing chamber 120, wherein the sample fluid is flowed at a rate slow enough that the cells are not pushed out of cell processing chamber 120. Particularly, the motion of the actuated microposts 124 acts as an impeller to keep the cells suspended in cell processing chamber 120.

At a step 1020, a cell wash cycle is performed by flowing wash buffer solution through cell processing chamber 120 while microposts 124 are actuated, wherein the wash buffer solution is flowed at rate slow enough that the cells are not pushed out of cell processing chamber 120. For example, with microposts 124 actuated, a cell wash cycle is performed by flowing a volume of wash buffer solution 314 out of wash reservoir 132, flushing through cell processing chamber 120, and then collected in waste reservoir 134, wherein the wash buffer solution is flowed at a rate slow enough that the cells are not pushed out of cell processing chamber 120. Particularly, the motion of the actuated microposts 124 acts as an impeller to keep the cells suspended in cell processing chamber 120.

At a step 1025, a cell culture cycle is performed by flowing cell culture media through cell processing chamber 120 while microposts 124 are actuated, wherein the cell culture media is flowed at rate slow enough that the cells are not pushed out of cell processing chamber 120. For example, with microposts 124 actuated, a cell culture cycle is performed by flowing a volume of cell culture media out of cell culture media reservoir 133, filling cell processing chamber 120, wherein the wash buffer solution is flowed at a rate slow enough that the cells are not pushed out of cell processing chamber 120. Particularly, the motion of the actuated microposts 124 acts as an impeller to keep the cells suspended in cell processing chamber 120.

At a step 1030, a cell counting operation is performed to determine the number of cells in cell processing chamber 120. For example, while microposts 124 are actuated and while cells 312 are suspended in cell processing chamber 120, counting mechanism 162 is activated to determine the number of cells 312 in cell processing chamber 120. In one example, counting mechanism 162 is an optical imaging system that uses a digital camera and image analysis processes to count the cells 312. Counting cells in suspension may be achieved via optical density (also called turbidity) measurement, a zetasizer-style measurement (where cells are electrokinetically moved and a laser counts cells as they pass by), or any other means for measuring cell count of suspended cells.

At a step 1035, a cell recovery cycle is performed by flowing wash buffer solution through cell processing chamber 120 while actuating microposts 124, wherein the wash buffer solution is flowed at rate fast enough that the cells are pushed out of cell processing chamber 120. For example, a cell recovery cycle is performed by flowing wash buffer solution 314 through cell processing chamber 120 while at the same time actuating microposts 124 (via actuation mechanism 160), wherein the wash buffer solution is flowed at rate fast enough that the cells are pushed out of cell processing chamber 120. The resulting cell-containing eluent flows out of cell processing chamber 120 and is collected in eluent reservoir 136.

Figure 21:
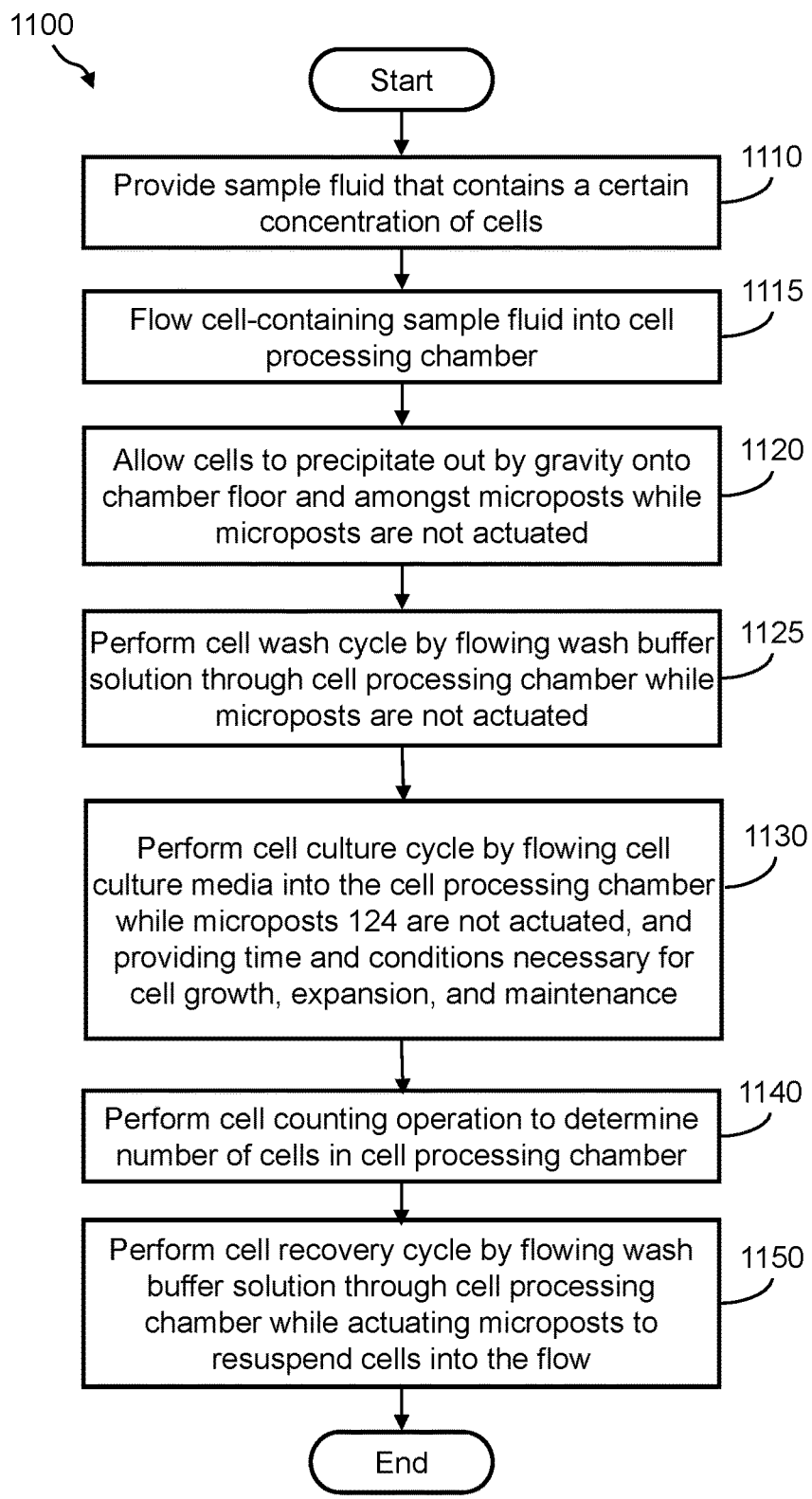
FIG. 21 illustrates a flow diagram of an example of a method of using the presently disclosed cell processing system to collect, wash, culture, count, and recover cells.

FIG. 21 illustrates a flow diagram of an example of a method 1100 of using the presently disclosed cell processing system 100 to collect, wash, culture, and recover cells. Method 1100 may include, but is not limited to, the following steps.

At a step 1110, a sample fluid is provided that contains a certain concentration of cells. In one example, sample reservoir 130 is a 200 µL reservoir that is holding a 200 µL-sample produced using a centrifugation process. For example, previous to cell processing system 100, a 10 mL sample undergoes a cell concentration process by centrifugation to produce a cell pellet. Then, the cell pellet is resuspended into a 200 µL solution, which is then supplied to sample reservoir 130 of cell processing system 100. The concentration of this 200 µL-sample can be, for example, from about 1 cells/uL to about 10,000 cells/uL.

At a step 1115, the cell-containing sample fluid is flowed into cell processing chamber 120. For example and referring again to FIG. 8A, with microposts 124 not actuated, a volume of sample fluid 310 that contains cells 312 is flowed out of sample reservoir 130 and fills cell processing chamber 120.

At a step 1120, the cells are allowed time to precipitate out by gravity, microfluidic cell separator (e.g., see FIG. 16A and FIG. 16B), and/or dielectrophoresis (e.g., see FIG. 17) onto the chamber floor (i.e., the micropost substrate) and amongst microposts 124 while microposts 124 are not actuated. For example and referring again to FIG. 8A, with microposts 124 not actuated, cells 312 are allowed time to precipitate out by gravity onto the floor of cell processing chamber 120 and collect amongst microposts 124. In one example, the time allowed is from about 1 minute to about 2 minutes.

At a step 1125, a cell wash cycle is performed by flowing wash buffer solution through cell processing chamber 120 while microposts 124 are not actuated. For example and referring again to FIG. 8B, with microposts 124 not actuated, a cell wash cycle is performed by flowing a volume of wash buffer solution 314 out of wash reservoir 132, flushing through cell processing chamber 120, and then collected in waste reservoir 134. All the while, cells 312 are trapped amongst microposts 124 of micropost array 122 and thereby held inside cell processing chamber 120. This step can be repeated any number of times until the cells are suitably cleaned.

At step 1130, a cell culture cycle is performed by flowing cell culture media into cell processing chamber 120 while microposts 124 are not actuated and providing time and conditions necessary for cell growth, expansion, and maintenance.

At a step 1140, a cell counting operation is performed to determine the number of cells in cell processing chamber 120. For example, while microposts 124 are not actuated and while cells 312 are resting on the floor of cell processing chamber 120, counting mechanism 162 is activated to determine the number of cells 312 in cell processing chamber 120. In one example, counting mechanism 162 is an optical imaging system that uses a digital camera and image analysis processes to count the cells 312.

At a step 1150, a cell recovery cycle is performed by flowing wash buffer solution through cell processing chamber 120 while actuating microposts 124 to resuspend the cells into the flow. For example and referring again to FIG. 8C, a cell recovery cycle is performed by flowing wash buffer solution 314 through cell processing chamber 120 while at the same time actuating microposts 124 (via actuation mechanism 160) in order to resuspend cells 312 into the flow. Particularly, the motion of the actuated microposts 124 kicks cells 312 up and clear of microposts 124 and into the flow of wash buffer solution 314. The resulting cell-containing eluent flows out of cell processing chamber 120 and is collected in eluent reservoir 136.

As described above, many modifications and other embodiments of the presently disclosed subject matter set forth herein will come to mind to one skilled in the art to which the presently disclosed subject matter pertains having the benefit of the teachings presented in the foregoing descriptions and the associated Drawings. For example, in embodiments in which cells are allowed to precipitate onto the micropost substrate amongst the surface-attached microposts, some cells are naturally more adherent than other cells and the cell collection step may require inclusion of an agent in the wash media that causes cells to detach (e.g., trypsin). In other embodiments, it may be desired to collect the eluent without collecting the cells, for example to collect eluent from cells that have been cultured in cell processing chamber 120, where the cultured cells produce proteins, peptides, and the like that are released into the eluent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A cell processing system comprising:
   a fluidics cartridge comprising:
   a cell processing chamber comprising a bottom substrate and a top substrate separated by the gap, wherein the cell processing chamber further comprises a micropost array, wherein the micropost array comprises a plurality of surface-attached microposts arranged on a micropost substrate, and wherein the micropost substrate is positioned atop the bottom substrate; and
   a control instrument;
   wherein the surface-attached posts are configured for actuation in the presence of an actuation force, wherein no binding agents are disposed on or integrated with the surface-attached posts, the bottom substrate, the top substrate, or the micropost substrate, and wherein the bottom substrate and the top substrate are arranged atop a registration feature configured for mounting on the control instrument.

2. The cell processing system of claim 1, wherein the fluidics cartridge further comprises one or more sample reservoirs, one or more wash reservoirs, one or more supply cell processing chambers, one or more waste reservoirs, and one or more eluent reservoirs fluidly connected via an arrangement of fluid channels to the cell processing chamber.

3. The cell processing system of claim 2, wherein a fluid control port is provided in each of the fluid channels.

4. The cell processing system of claim 3, wherein the one or more sample reservoirs, the one or more wash reservoirs, the one or more supply cell processing chambers, the one or more waste reservoirs, and the one or more eluent reservoirs each comprise an inlet and an outlet.

5. The cell processing system of claim 4, wherein a fluid control port is provided at the outlet of the sample reservoir, a fluid control port is provided at the outlet of the wash reservoir, a fluid control port is provided at the inlet of the waste reservoir, and a fluid control port is provided at the inlet of the eluent reservoir.

6. The cell processing system of claim 5, wherein the fluid control ports comprise pinch valves.

7. The cell processing system of claim 6, wherein a first pump is fluidly connected to the sample reservoir and a second pump is fluidly connected to the wash reservoir.

8. The cell processing system of claim 7, wherein the first pump and the second pump are capable of supplying positive pressure and negative pressure to the cell processing chamber.

9. The cell processing system of claim 1, wherein the control instrument comprises a platform configured to interface with the fluidics cartridge.

10. The cell processing system of claim 9, wherein the platform comprises a plurality of fluid control ports positioned to correspond to the fluid channels of the fluidics cartridge.

11. A method for processing cells comprising the use of a cell processing system of claim 1, comprising the steps of:
   (a) introducing a sample fluid to a sample reservoir, wherein the sample fluid comprises cells, and wherein the cells are suspended in the sample fluid;
   (b) flowing the sample fluid into the cell processing chamber;
   (c) precipitating the cells suspended in the sample fluid onto the micropost substrate amongst the surface-attached microposts, wherein no actuation forces are applied to the surface-attached microposts;

(d) performing a cell wash cycle comprising flowing wash buffer solution out of the wash reservoir, through cell processing chamber, and into a waste reservoir, wherein the cells remain precipitated onto the micropost substrate amongst the surface-attached microposts, and wherein no actuation forces are applied to the surface-attached microposts;

(e) repeating step (d) as needed to wash the cells precipitated onto the micropost substrate amongst the surface-attached microposts;

(f) performing a cell recovery cycle comprising flowing wash buffer solution through the cell processing chamber, wherein actuation forces are applied to the surface-attached microposts to resuspend the cells into the flowing wash buffer solution, thereby producing a cell-containing eluent; and (g) flowing the cell-containing eluent into an eluent reservoir.

12. A method for processing cells comprising the use of a cell processing system of claim 1, comprising the steps of:

(a) introducing a sample fluid to a sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell lysis cycle, wherein actuation forces are applied to the surface-attached microposts to produce a beating motion by the surface-attached microposts, thereby producing a lysed cell-containing eluent; and (e) flowing the lysed cell-containing eluent into an eluent reservoir.

13. A method for processing cells comprising the use of a cell processing system of claim 1, comprising the steps of:

(a) introducing a sample fluid to the sample reservoir, wherein the sample fluid comprises cells, and wherein the cells are suspended in the sample fluid;

(b) flowing the sample fluid into the cell processing chamber while the surface-attached microposts are actuated, wherein the sample fluid is flowed at rate slow enough that the cells are not pushed out of the cell processing chamber;

(c) performing a cell wash cycle comprising flowing wash buffer solution out of a wash reservoir into the cell processing chamber, wherein actuation forces are applied to the surface-attached microposts, and further wherein the wash buffer solution is flowed at a rate slow enough that the cells are not pushed out of the cell processing chamber;

(d) performing a cell culture cycle comprising flowing cell culture media out of a cell culture media reservoir into the cell processing chamber, wherein actuation forces are applied to the surface-attached microposts, and further wherein the cell culture media is flowed at a rate slow enough that the cells are not pushed out of the cell processing chamber;

(e) performing a cell recovery cycle comprising flowing wash buffer solution through the cell processing chamber, wherein actuation forces are applied to the surface-attached microposts, and further wherein the wash buffer solution is flowed at a rate fast enough that the cells are not pushed out of the cell processing chamber; and (f) flowing the cell-containing eluent into an eluent reservoir.

14. A method for processing cells comprising the use of a cell processing system of claim 1, comprising the steps of:

(a) introducing a sample fluid to a sample reservoir, wherein the sample fluid comprises cells, and wherein the cells are suspended in the sample fluid;

(b) flowing the sample fluid into the cell processing chamber;

(c) precipitating the cells suspended in the sample fluid onto the micropost substrate amongst the surface-attached microposts, wherein no actuation forces are applied to the surface-attached microposts;

(d) performing a cell wash cycle comprising flowing wash buffer solution out of a wash reservoir, through cell processing chamber, and into a waste reservoir, wherein the cells remain precipitated onto the micropost substrate amongst the surface-attached microposts, and wherein no actuation forces are applied to the surface-attached microposts;

(e) repeating step (d) as needed to wash the cells precipitated onto the micropost substrate amongst the surface-attached microposts;

(f) performing a cell culture cycle by flowing cell culture media into cell processing chamber while microposts are not actuated and providing time and conditions necessary for cell growth, expansion, and maintenance;

(g) performing a cell recovery cycle comprising flowing wash buffer solution through the cell processing chamber, wherein actuation forces are applied to the surface-attached microposts to resuspend the cells into the flowing wash buffer solution, thereby producing a cell-containing eluent; and (h) flowing the cell-containing eluent into an eluent reservoir.

15. The method of claim 14, further comprising the step of performing a cell counting operation with the cell counting mechanism to determine the number of cells in the cell processing chamber, wherein the cell counting operation is performed before the cell recovery cycle step.

16. The method of claim 15, wherein the sample fluid comprises cells comprising clumps of cells, wherein the cells comprising clumps of cells are suspended in the sample fluid, and wherein step (b) further comprises applying actuation forces to the surface-attached microposts to break up the clumps of cells.

17. The method of claim 16, wherein prior to step (a), the sample fluid is produced by a cell concentration process comprising centrifuging a sample comprising cells to produce a cell pellet, followed by resuspending cells in the cell pellet in solution to produce the sample fluid.

18. The cell processing system of claim 1, further comprising a microarray on the top substrate opposing the microposts, wherein the microarray is functionalized with analyte capture elements.

19. The cell processing system of claim 1, further comprising a cell concentration module.

20. A method for processing cells comprising the use of a cell processing system of claim 19, comprising the steps of:

(a) introducing a sample fluid to a sample reservoir, wherein the sample fluid comprises cells, and wherein the cells are suspended in the sample fluid;

(b) flowing the sample fluid into the cell concentration module and performing a cell concentration process to produce a concentrated sample fluid; and (c) flowing the concentrated sample fluid into the cell processing chamber for further processing.

21. The cell processing system of claim 1, wherein the micropost array comprises a flow path formed by the absence of microposts.

22. The cell processing system of claim 21, wherein at least some portion of the flow path is curved and configured to aggregate cells at the outside of curves such that the cells precipitate and/or are pushed into the microposts.

23. The cell processing system of claim 1, wherein the micropost array comprises arrangements of micropost barriers configured to trap cells such that the cells precipitate and/or are pushed into the microposts.

24. The cell processing system of claim 1, further comprising features on the top substrate opposing the microposts, wherein the features are configured to assist cells to precipitate out of solution and/or facilitate microfluidic cell separation.

25. The cell processing system of claim 1, further comprising one or more electrodes provided in the bottom substrate, the top substrate, or both the bottom substrate and the top substrate.

\* \* \* \* \*